(12) United States Patent     (10) Patent No.: US 10,640,828 B2
Bevilacqua et al.     (45) Date of Patent: May 5, 2020

(54) LOW SEQUENCE BIAS SINGLE-STRANDED DNA LIGATION

(71) Applicant: The Penn State Research Foundation, University Park, PA (US)

(72) Inventors: Philip C. Bevilacqua, State College, PA (US); Sarah M. Assmann, State College, PA (US); Yiliang Ding, State College, PA (US); Chun Kit Kwok, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 249 days.

(21) Appl. No.: 15/785,680

(22) Filed: Oct. 17, 2017

(65) Prior Publication Data

US 2018/0030494 A1     Feb. 1, 2018

Related U.S. Application Data

(62) Division of application No. 14/151,491, filed on Jan. 9, 2014, now Pat. No. 9,816,120.

(60) Provisional application No. 61/750,469, filed on Jan. 9, 2013.

(51) Int. Cl.
    *C12Q 1/6876*     (2018.01)
    *C12P 19/34*     (2006.01)
    *C12Q 1/6806*     (2018.01)
    *C12N 15/66*     (2006.01)
    *C12N 15/10*     (2006.01)

(52) U.S. Cl.
CPC ......... *C12Q 1/6876* (2013.01); *C12N 15/10* (2013.01); *C12N 15/66* (2013.01); *C12P 19/34* (2013.01); *C12Q 1/6806* (2013.01); *C12Y 605/01001* (2013.01)

(58) Field of Classification Search
None
See application file for complete search history.

(56) References Cited

U.S. PATENT DOCUMENTS

| | | |
|---|---|---|
| 5,215,899 A | 6/1993 | Dattagupta |
| 6,416,950 B1 | 7/2002 | Lohse et al. |
| 2004/0115643 A1 | 6/2004 | Lizardi et al. |
| 2007/0020644 A1 | 1/2007 | Kolykhalov et al. |
| 2007/0111226 A1 | 5/2007 | Tan et al. |
| 2007/0269825 A1 | 11/2007 | Wang et al. |
| 2008/0194416 A1 | 8/2008 | Chen |

OTHER PUBLICATIONS

Eiko Ohtsuka et al., "Joining of Synthetic Ribotrinucleotides with Defined Sequences Catalyzed by T4 RNA Ligase," *Eur. J. Biochem*, 1977, 81:285-291.

(Continued)

*Primary Examiner* — Samuel C Woolwine
(74) *Attorney, Agent, or Firm* — Riverside Law LLP

(57) ABSTRACT

The invention provides compositions and methods for ligating single stranded nucleic acids wherein the ligation is based on fast, efficient, and low-sequence bias hybridization of an acceptor molecule with a donor molecule. In one embodiment, the structure of the donor molecule comprises a stem-loop intramolecular nucleotide base pairing (i.e., hairpin) and a 3'-overhang region such that the overhang is able to hybridize to nucleotides present in the 3' end of the acceptor molecule.

9 Claims, 28 Drawing Sheets

Specification includes a Sequence Listing.

(56) References Cited

OTHER PUBLICATIONS

Elena Romaniuk et al., "The Effect of Acceptor Oligoribonucleotide Sequence on the $T_4$ RNA Ligase Reaction," *Eur. J. Biochem*, 1982, 125:639-643.

Kazudo Harada et al., "In vitro selection of optimal DNA substrates for T4 ligase," *Proc. Natl Acad. Sci*, 1993, 90:1576-1579.

Xing-Hai Zhang et al., "Single-stranded DNA ligation by T4 RNA ligase for PCR cloning of 5'-noncoding fragments and coding sequence of specific gene," *Nucleic Acids Research*, 1996, 24(5):990-991.

Shu-Mei Dai et al., "Ligation-mediated PCR for quantitative in vivo footprinting," *Nature Biotechnology*, 2000, 18:1108-1111.

Michael Zuker, "Mfold web server for nucleic acid folding and hybridization prediction," *Nucleic Acids Research*, 2003, 31(13):3406-3415.

Thorarinn Blondal et al., "Isolation and characterization of a thermostable RNA ligase 1 from a *Thermus scotoductus* bacteriophage TS2126 with good single-stranded DNA ligation properties," *Nucleic Acids Research*, 2005, 33(1):135-142.

Tian W. Li et al., "Structure-independent and quantitative ligation of single-stranded DNA," *Analytical Biochemistry*, 2006, 349:242-246.

Sam Ev Linsen et al., "Limitations and possibilities of small RNA digital gene expression profiling," *Nature Methods*, 2009, 6(7):474-476.

Joshua Z. Levin et al., "Comprehensive comparative analysis of strand-specific RNA sequencing methods," *Nat Methods*, 2010, 7(9):709-715.

Anitha D. Jayaprakash et al., "Identification and remediation of biases in the activity of RNA ligases in small-RNA deep sequencing," *Nucleic Acids Research*, 2011, 39(21):1-12.

Julius B. Lucks et al., "Multiplexed RNA structure characterization with selective 2'-hydroxyl acylation analyzed by primer extension sequencing (SHAPE-Seq)," *PNAS*, 2011, 108(27):11063-11068.

Kevin P McCormick et al., "Experimental design, preprocessing, normalization and differential expression analysis of small RNA sequencing experiments," *Silence*, 2011, 2:2, pp. 1-19.

Anna Potapova et al., "Systemic cross-validation of 454 sequencing and pyrosequencing for the exact quantification of DNA methylation patterns with single CpG resolution," *BMC Biotechnology*, 2011, 11:6, pp. 1-10.

Eunkyoo Oh et al., "Interaction between BZR1 and PIF4 integrates brassinosteroid and environmental responses," *Nat Cell Biol.*, 2012, 14(8):802-809.

Agata Fratczak et al., "LNA-Modified Primers Drastically Improve Hybridization to Target RNA and Reverse Transcription," *Biochemistry*, 2009, 48:514-516.

Renate Rieder et al., "Enzymatic Ligation Strategies for the Preparation of Purine Riboswitches with Site-Specific Chemical Modifications," *Methods in Molecular Biology*, 2009, 540:15-24.

Zhanyong Shu et al., "Isolation and Characterization of Thermodynamically Stable and Unstable RNA Hairpins from a Triloop Combinatorial Library," *Biochemistry*, 1999, 38:15369-15379.

Daniel C. Tessier et al., "Ligation of Single-Stranded Oligodeoxyribonucleotides by T4 RNA Ligase," *Analytical Biochemistry*, 1986, 158:171-178.

Oladapo Yeku et al., "Rapid Amplification of cDNA Ends (RACE)," *Methods in Molecular Biology*, 2011, 703:107-122.

Vologodskii, "Biophysics of DNA", Cambridge University Press (2015) pp. 37-39.

Cherepanov et al., "Joining of short DNA oligonucleotides with base pair mismatches by T4 DNA ligase", Journal of Biochemistry, vol. 129:pp. 61-28 (2001).

| Name | Length | 5' | Sequence (5'-3') | 3' |
|---|---|---|---|---|
| "A" Acceptor | 24 | Cy5 | GAA CCG GAC CGA AGC CCG ATT TGA (SEQ ID NO: 1) | OH |
| "G" Acceptor | 24 | Cy5 | GAA CCG GAC CGA AGC CCG ATT TGG (SEQ ID NO: 2) | OH |
| "C" Acceptor | 24 | Cy5 | GAA CCG GAC CGA AGC CCG ATT TGC (SEQ ID NO: 3) | OH |
| "T" Acceptor | 24 | Cy5 | GAA CCG GAC CGA AGC CCG ATT TGT (SEQ ID NO: 4) | OH |
| Donor oligo 2 | 26 | p | CTG CTG ATC ACC GAC TGC CCA TAG AG (SEQ ID NO: 5) | C3 |
| Donor oligo 3 | 29 | p | NNN CTG CTG ATC ACC GAC TGC CCA TAG AG (SEQ ID NO: 6) | C3 |
| WT and M6 donor | 33 | p | TGA AGA GCT GCT GAT CAC CGA CTG CCC ATA GAG (SEQ ID NO: 7) | C3 |
| M1 and M4 donor | 33 | p | TGA AGA GCT GCT GAT CAA CGA CTG CCC ATA GAG (SEQ ID NO: 8) | C3 |
| M2 and M7 donor | 33 | p | TGA AGA GCT GCT GAT CAG CGA CTG CCC ATA GAG (SEQ ID NO: 9) | C3 |
| M3 and M5 donor | 33 | p | TGA AGA GCT GCT GAT CAT CGA CTG CCC ATA GAG (SEQ ID NO: 10) | C3 |
| M8 donor | 33 | p | AGA AGA GCT GCT GAT CTC CGA CTG CCC ATA GAG (SEQ ID NO: 11) | C3 |
| M9 donor | 33 | p | GGA AGA GCT GCT GAT CCC CGA CTG CCC ATA GAG (SEQ ID NO: 12) | C3 |
| M10 donor | 33 | p | CGA AGA GCT GCT GAT CGC CGA CTG CCC ATA GAG (SEQ ID NO: 13) | C3 |
| M11 donor | 33 | p | AGA AGA GCT GCT GAT CTC CGA CTG CCC ATA GAG (SEQ ID NO: 14) | C3 |
| M12 donor | 33 | p | TGA AGA GCT GCT GAT CTC CGA CTG CCC ATA GAG (SEQ ID NO: 15) | C3 |
| M13 donor | 33 | p | TGA TGA GCT GCT GAT CAC CGA CTG CCC ATA GAG (SEQ ID NO: 16) | C3 |
| M14 donor | 33 | p | TGA CGA GCT GCT GGT CAC CGA CTG CCC ATA GAG (SEQ ID NO: 17) | C3 |
| M15 donor | 33 | p | TGA AGA GCT GCT GTT CAC CGA CTG CCC ATA GAG (SEQ ID NO: 18) | C3 |
| M16 donor | 33 | p | TGA AGA GCT GCT GTT CAG CGA CTG CCC ATA GAG (SEQ ID NO: 19) | C3 |
| M17 donor | 21 | p | TGA AGA GCT GCT GTT CAC CGA (SEQ ID NO: 20) | C3 |
| M18 donor | 26 | p | TGA AGA GCC TAG TCG CTG TTC ACC GA (SEQ ID NO: 21) | C3 |
| Optimized hairpin donor | 40 | p | TGA AGA GCC TAG TCG CTG TTC ANN NNN NCT GCC CAT AGA G (SEQ ID NO: 22) | C3 |
| FAM 1 acceptor | 16 | FAM | CGG CGA ACC GGA TCG A (SEQ ID NO: 23) | OH |
| FAM 2 acceptor | 19 | FAM | TTG TGA CAC CCA GGC AGA C (SEQ ID NO: 24) | OH |
| FAM 3 acceptor | 21 | FAM | CCA GAA GGC TTG GGG CGC AAC (SEQ ID NO: 25) | OH |
| 91mer Acceptor | 91 | OH | TTC ACA ATC GCA GAA GCT CTC TCG CAG TCC CCT TCC CCT TCC CTC CCA ATT TTT AAA AGA AAA TAA AAT CCT ATA GTG AGT CGT ATT A (SEQ ID NO: 26) | OH |

Figure 23

LOW SEQUENCE BIAS SINGLE-STRANDED DNA LIGATION

CROSS-REFERENCE TO RELATED APPLICATIONS

This application is a divisional application of U.S. patent application Ser. No. 14/151,491, filed Jan. 9, 2014, which claims priority to U.S. Provisional Patent Application No. 61/750,469 filed Jan. 9, 2013, the contents of which are incorporated by reference herein in their entirety.

BACKGROUND OF THE INVENTION

Intermolecular single-stranded DNA (ssDNA) ligation is important for various biotechnical applications, such as LMPCR (Zhang et al., 1996, Nucleic Acids Res. 24:990-991; Dai et al., 2000, Nat. Biotech. 18:1108-1111; Yeku and Frohman, 2011, Methods Mol. Biol. 703:107-122) and cDNA library construction (Levin et al., 2010, Nat. Meth. 7:709-715; Lucks et al., 2011, Proc. Natl. Acad. Sci. USA 108:11063-11068), each of which require a fixed sequence DNA oligonucleotide to ligate to an unknown 3'-end of a cDNA. Currently, only a few protocols are available to perform such intermolecular ssDNA ligations, which use Circligase I (Lucks et al., 2011, Proc. Natl. Acad. Sci. USA 108:11063-11068; Li et al., 2006, Anal. Biochem. 349:242-246; Blondal et al., 2005, Nucleic Acids Res. 33:135-142) or T4 RNA ligase I (Zhang et al., 1996, Nucleic Acids Res. 24:990-991; Tessier et al., 1986, Anal. Biochem. 158:171-178). In addition, Circligase II recently became commercially available; however Circligase II is identical to Circligase I, differing only in the level of protein adenylation. The nucleotide preferences, referring to the likelihood of ligation to a certain base (given an equal concentration of the 4 bases in the reaction mixture), of these ligation methods on intermolecular ssDNA ligations, however, were not available prior to the present invention.

Identification and remediation of nucleotide bias in ssDNA ligation is crucial because such bias can fail to quantitatively capture the original information stored in the DNA sample. Indeed, nucleotide preference in nucleic acid ligations can potentially lead to misinterpretation of gene expression levels (Jayaprakash et al., 2011, Nucleic Acids Res. 39(21):e141; McCormick et al., 2011, Silence 2(1):2; Linsen, et al., 2009, Nat. Meth. 6:474-476). Nucleotide bias and inefficiencies of ssDNA ligation hampers ligation methods currently in use.

Thus, there is a need in the art for compositions and methods providing fast, efficient, and low-sequence bias ligation of ssDNAs. The present invention satisfies this unmet need.

SUMMARY OF THE INVENTION

The invention provides a method of producing a ligated single stranded nucleic acid molecule. In one embodiment, the method comprises: a) contacting a single-stranded acceptor nucleic acid molecule with a donor nucleic acid molecule, wherein the donor nucleic acid molecule comprises one or more nucleic acids having a stem region and a single-stranded 3' terminal overhang region; b) hybridizing the single stranded 3' terminal overhang region of the donor nucleic acid molecule to the acceptor molecule thereby forming an acceptor-donor hybrid molecule comprising a nick or gap between the acceptor nucleic acid and donor nucleic acid molecule; c) and ligating the 5' end of the donor nucleic acid molecule to the 3' end of the acceptor nucleic acid molecule thereby generating a ligated product.

In one embodiment, the ligation step is accomplished after the hybridization, wherein the hybridization step positions the acceptor and donor molecule in a way that ligation occurs under conditions that allow for ligation between the 5' end of the donor nucleic acid molecule and the 3' end of the acceptor nucleic acid molecule.

In one embodiment, the ligation occurs by enzymatic means. In another embodiment, the enzymatic means comprises using DNA ligase. In yet another embodiment, the DNA ligase is T4 DNA ligase.

In one embodiment, the ligation occurs by chemical means.

In one embodiment, the 3' terminal overhang region of donor molecule comprises at least 1 bases.

In one embodiment, the stem region of the donor molecule is double stranded and comprises at least 4 nucleotide pairs. In another embodiment, the stem region comprises at least one mismatched pair.

In one embodiment, the donor molecule further comprises a loop structure, wherein the loop structure comprises at least 2 bases. In another embodiment, the loop structure comprises a portion of a primer binding site.

The invention also provides a composition comprising a donor nucleic acid molecule, wherein the molecule comprises a stem-loop structure and a 3' overhang, further wherein the molecule comprises a continuous primer binding site that encompasses a portion of the stem and a portion of the loop structure.

In one embodiment, the stem portion of the stem-loop structure comprises at least 3 nucleotide base pairs and at least one mismatch pair.

In one embodiment, the 3' overhang comprises at least 4 nucleotides.

In one embodiment, the primer binding site comprises 8 nucleotides.

In one embodiment, the donor molecule is hybridized to a single stranded nucleic acid acceptor molecule to form a hybridized molecule comprising the donor molecule and the acceptor molecule.

In one embodiment, the hybridized molecule is stable at a temperature as high as 65° C.

The invention also provides a kit comprising a donor nucleic acid molecule. In one embodiment, the molecule comprises a stem-loop structure and a 3' overhang, further wherein the molecule comprises a continuous primer binding site that encompasses a portion of the stem and a portion of the loop structure.

In one embodiment, the kit comprises a DNA ligase. In one embodiment, the DNA ligase is T4 DNA ligase.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts the design of the ssDNA ligation assay. Mfold-predicted secondary structure of the acceptor and donor. FIG. 1B through FIG. 1D depict the nucleotide preference of ligations performed using Circligase I, T4 RNA ligase I, and initial tests of T4 DNA ligase, respectively. FIG. 1B and FIG. 1C represent prior methods of ssDNA ligation, while FIG. 1D is the initial version of the method developed herein. Lanes labeled 'A', 'G', 'C', and 'T' refer to the identity of the 3' end nucleotide of the acceptor, which differs in each lane as indicated. Samples were fractionated on 10% urea-polyacrylamide gels and subjected to PhosphorImager scanning. Reaction conditions are described in detail elsewhere herein. Below each gel, the proposed mode of reaction of the corresponding ligase is provided; note that only the method depicted in FIG. 1D is template-mediated.

FIG. 3A through FIG. 3C, depicts the results of experiments demonstrating ssDNA ligation and kinetics. FIG. 3A depicts the design of nucleotide preference ligation using the optimized donor (40mer) that contains a random hexamer templating region (N6) and an acceptor (24mer). SEQ ID NO: 29 represents the depicted portion of the donor molecule. The 7 nt SapI/BspQI site is in bold. FIG. 3B is an image depicting the ssDNA ligation result using the optimized donor from panel 3A. Lane labels 'A', 'G', 'C', and 'T' refer to the DNA base of the 3' end nucleotide of the acceptor. The % yields reported are the average of three trials, with standard deviation indicated. FIG. 3C is a graph depicting the kinetics of nucleotide preference for ssDNA ligation. Data points are the average of three trials, and error bars are standard deviations.

FIG. 5A and FIG. 5B, depicts the results of experiments examining ligation-mediated PCR using the optimized hairpin donor construct and a 91 nucleotide acceptor, followed by SapI/BspQI restriction digestion. FIG. 5A depicts the results of experiments where the ssDNA ligation was performed as described in FIG. 4, except that 1 pmol of 91mer acceptor was used and the reaction was conducted for 0.5 h. The control lanes did not have T4 DNA ligase added. Thirty rounds of PCR were carried out using New England Biolabs Taq DNA polymerase with varying annealing temperatures as indicated. The PCR primers were complementary to the 5'-end of the acceptor and the fixed region of the donor. SapI or BspQI digestion was performed on the 131 bp PCR product using NEB buffer 4 under the vendor's recommended condition. The digestion was completed and a product of 87/91 bp was observed after 1 h reaction for both enzymes. Shown is an ethidium bromide-stained agarose gel. FIG. 5B depicts a general scheme for LMPCR and restriction digest. SEQ ID NO: 29 represents the depicted portion of the donor molecule.

FIG. 15A through FIG. 15C, depicts the results of ssDNA ligation kinetics of WT donor and "G" acceptor under standard and optimized conditions using T4 DNA ligase. FIG. 15A is an image depicting the ligation time course for standard conditions. FIG. 15B is an image depicting the ligation time course for optimized conditions. FIG. 15C is a ssDNA ligation kinetics plot. Standard ligation conditions contained 100 pmol of 5'p donor, 1 pmol of Cy5-labelled acceptor, 50 mM Tris-HCl (pH 7.5), 10 mM $MgCl_2$, 10 mM DTT, 1 mM ATP, and 15 U laboratory preparation of T4 DNA ligase at 16° C. Optimized ligation conditions added 20% PEG 8000 and 0.5 M betaine.

FIG. 23 depicts the DNA sequence information for constructs used herein.

FIGS. 24A through 24C, is a schematic of a general design for the acceptor, donor, and hybrid molecule of the invention. FIG. 24A depicts a schematic of the acceptor molecule whereby the nucleic acid molecule can comprise any base and be of any length. FIG. 24B depicts a schematic of the donor molecule having a stem structure, a loop region, and a 3'-overhang. FIG. 24C depicts a schematic of the unligated hybrid molecule comprising a nick. The hybrid molecule comprises a larger and more stable stem structure than was present in the donor alone.

DETAILED DESCRIPTION

Figure 1A:
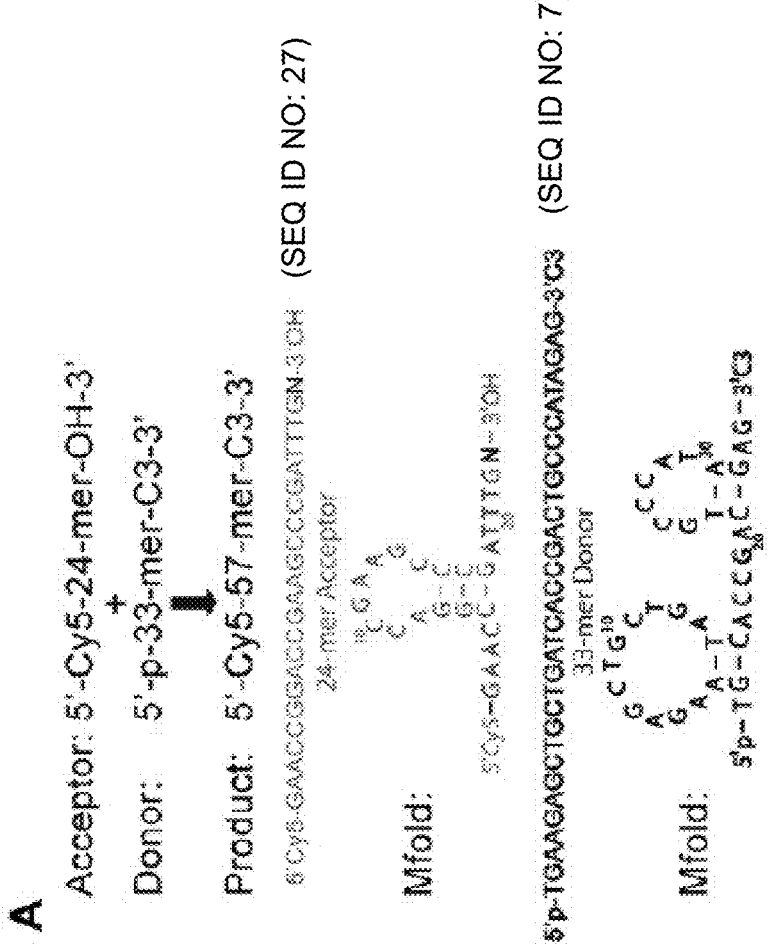
FIG. 1A through FIG. 1D, depicts the results of experiments examining ssDNA ligation by different ligases.

The present invention is based on the development of a rational experimental design to remove the inherent nucleotide bias and inefficiencies in ligation methods currently in use. The invention is based on a novel hybridization-based strategy that allows for fast, efficient and low-sequence bias ligation of two single stranded DNAs (ssDNA). Accordingly, the invention provides a method of ligating single stranded nucleic acids that overcomes the nucleotide bias and inefficiencies associated with currently used protocols.

In one embodiment, the method of the invention comprises a ligation approach that is based on hybridization of at least two single stranded nucleic acids, one of the single stranded nucleic acid is referred herein as an acceptor molecule and the other single stranded nucleic acids is referred herein as a donor molecule.

In some instances, the donor molecule comprises a hairpin structure. In other instances, the hairpin donor molecule comprises a 3'-overhang. In one embodiment, the ligation between the acceptor molecule and the donor molecule is accomplished through the actions of a ligase. In certain embodiments, the ligase is a T4 DNA ligase. Generally, the donor molecule hybridizes with an acceptor 3'-end to yield the desired ligation product (e.g., a hybrid molecule comprising the acceptor and donor molecule).

The ability to ligate single stranded nucleic acids provides a valuable technique that can be applied to various protocols, including, those protocols studying nucleic acids.

The ssDNA ligation composition and method of the present invention may be used in a wide variety of protocols and technologies. For example, in certain embodiments, ssDNA ligation is used in the fields of molecular biology, genomics, transcriptomics, epigenetics, nucleic acid sequencing, and the like. In one embodiment, ssDNA ligation may be used in any technology that may require or benefit from the ligation of ssDNA.

In one embodiment, the ssDNA ligation composition and method of the invention is applicable to DMS/SHAPE-LMPCR and Structure-Seq, and DMS-seq to obtain in vivo or in vitro RNA structural data at nucleotide resolution in low-abundance transcripts and genome-wide, respectively in any organism or tissue.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Amplification" refers to any means by which a polynucleotide sequence is copied and thus expanded into a larger number of polynucleotide molecules, e.g., by reverse transcription, polymerase chain reaction, and ligase chain reaction, among others. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

"Homologous, homology" or "identical, identity" as used herein, refer to comparisons among amino acid and nucleic acid sequences. When referring to nucleic acid molecules, "homology," "identity," or "percent identical" refers to the percent of the nucleotides of the subject nucleic acid sequence that have been matched to identical nucleotides by a sequence analysis program. Homology can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the ExPaSy is used to align sequence fragments of genomic DNA sequences. However, equivalent alignment assessments can be obtained through the use of any standard alignment software.

As used herein, "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC 3' and 5'TATGGC 3' share 50% homology.

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

The term "hybridization" refers to the process in which two single-stranded nucleic acids bind non-covalently to form a double-stranded nucleic acid; triple-stranded hybridization is also theoretically possible. Complementary sequences in the nucleic acids pair with each other to form a double helix. The resulting double-stranded nucleic acid is a "hybrid." Hybridization may be between, for example, two complementary or partially complementary sequences. The hybrid may have double-stranded regions and single stranded regions. The hybrid may be, for example, DNA: DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

The stability of a hybrid depends on a variety of factors including the length of complementarity, the presence of mismatches within the complementary region, the temperature and the concentration of salt in the reaction. Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) or 100 mM MES, 1 M Na, 20 mM EDTA, 0.01% Tween-20 and a temperature of 25-50° C. are suitable for allele-specific probe hybridizations. In a particularly preferred embodiment, hybridizations are performed at 40-50° C. Acetylated BSA and herring sperm DNA may be added to hybridization reactions. Hybridization conditions suitable for microarrays are described in the Gene Expression Technical Manual and the GeneChip Mapping Assay Manual available from Affymetrix (Santa Clara, Calif.).

A first oligonucleotide anneals with a second oligonucleotide with "high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 2012, Molecular Cloning: A Laboratory Manual, Cold Spring Harbor Laboratory Press, Cold Spring Harbor, N.Y.).

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolate" refers to a nucleic acid obtained from an individual, or from a sample obtained from an individual. The nucleic acid may be analyzed at any time after it is obtained (e.g., before or after laboratory culture, before or after amplification.)

The term "label" as used herein refers to a luminescent label, a light scattering label or a radioactive label. Fluorescent labels include, but are not limited to, the commercially available fluorescein phosphoramidites such as Fluoreprime (Pharmacia), Fluoredite (Millipore) and FAM (ABI). See U.S. Pat. No. 6,287,778.

As used herein, the term "ligation agent" can comprise any number of enzymatic or non-enzymatic reagents. For example, ligase is an enzymatic ligation reagent that, under appropriate conditions, forms phosphodiester bonds between the 3'-OH and the 5'-phosphate of adjacent nucleotides in DNA molecules, RNA molecules, or hybrids. Temperature sensitive ligases, include, but are not limited to, bacteriophage T4 ligase and *E. coli* ligase. Thermostable ligases include, but are not limited to, Afu ligase, Taq ligase, Tfl ligase, Tth ligase, Tth HB8 ligase, *Thermus* species AK16D ligase and Pfu ligase (see for example Published P.C.T. Application WO00/26381, Wu et al., Gene, 76(2): 245-254, (1989), Luo et al., Nucleic Acids Research, 24(15): 3071-3078 (1996). The skilled artisan will appreciate that any number of thermostable ligases, including DNA ligases and RNA ligases, can be obtained from thermophilic or hyperthermophilic organisms, for example, certain species of eubacteria and archaea; and that such ligases can be employed in the disclosed methods and kits. Further, reversibly inactivated enzymes (see for example U.S. Pat. No. 5,773,258) can be employed in some embodiments of the present teachings. Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in, among other places, Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowski, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); and U.S. Pat. No. 5,476,930.

The term "mismatch," "mismatch control" or "mismatch probe" refers to a nucleic acid whose sequence is not perfectly complementary to a particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

Conventional notation is used herein to describe polynucleotide sequences: the left-hand end of a single-stranded polynucleotide sequence is the 5'-end. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences." In the sequences described herein:

A=adenine,
G=guanine,
T=thymine,
C=cytosine,
U=uracil,
H=A, C or T/U,
R=A or G,
M=A or C,
K=G or T/U,
S=G or C,
Y=C or T/U,
W=A or T/U,
B=G or C or T/U,
D=A or G, or T/U,
V=A or G or C,
N=A or G or C or T/U.

The skilled artisan will understand that all nucleic acid sequences set forth herein throughout in their forward orientation, are also useful in the compositions and methods of the invention in their reverse orientation, as well as in their forward and reverse complementary orientation, and are described herein as well as if they were explicitly set forth herein.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with a detectable label, e.g., chromogenic, radioactive, or fluorescent moieties and used as detectable moieties. Examples of fluorescent moieties include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Other detectable moieties include digoxigenin and biotin.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes, so long as it does not interfere with hybridization. Thus, probes may be peptide nucleic acids in which the constituent bases are joined by peptide bonds rather than phosphodiester linkages. The term "match," "perfect match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe."

A "restriction site" is a portion of a double-stranded nucleic acid which is recognized by a restriction endonuclease. A portion of a double-stranded nucleic acid is "recognized" by a restriction endonuclease if the endonuclease is capable of cleaving both strands of the nucleic acid at a specific location in the portion when the nucleic acid and the endonuclease are contacted. Restriction endonucleases, their cognate recognition sites and cleavage sites are well known in the art. See, for instance, Roberts et al., 2005, Nucleic Acids Research 33:D230-D232.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, oligonucleotides and nucleic acids.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The invention provides compositions and methods for ligating single stranded nucleic acids wherein the ligation is based on hybridization of an acceptor molecule with a donor molecule that is fast, efficient, and has a low-sequence bias. In one embodiment of the invention, the structure of the donor molecule comprises a stem-loop intramolecular nucleotide base pairing (i.e., hairpin). Therefore, the donor molecule of the invention is sometimes referred herein as the hairpin donor molecule.

In one embodiment, the acceptor molecule comprises a hydroxyl group at its 3'-terminus and the donor molecule comprises a phosphate at its 5'-end. In this manner, the 5'-end of the donor molecule ligates with the 3'-terminal nucleotide of the acceptor molecule to yield the desired ligation product.

The present invention makes use of a hybridization-based strategy whereby a donor hairpin oligonucleotide is used to hybridize with an acceptor molecule. In one embodiment, the acceptor molecule can be of any sequence whereas the donor molecule is designed to form a hairpin structure that includes a 3'-overhang region such that the overhang on the hairpin oligonucleotide is able to hybridize to nucleotides present in the 3' end of the acceptor molecule. Preferably, the hairpin donor molecule having a 3'-overhang region such that the nucleotide(s) found in the 3'-overhang region of the hairpin oligonucleotide are complementary to the nucleotides found in the 3' end of the acceptor molecule thereby resulting in structure ready for closure by ligation by either enzymatic or chemical means.

Compositions

In one embodiment, the invention is a nucleic acid hairpin structure useful for ligating at least two single stranded nucleotides together. In another embodiment, the invention is a nucleic acid structure that is the result of ligating at least two single stranded nucleotides together. The ligation of two single stranded nucleotides involves combining a first single stranded nucleotide (e.g., acceptor molecule) with a second single stranded nucleotide (e.g., donor molecule), wherein the second single stranded nucleotide comprises a double stranded region and a single stranded region. The single stranded region found in the second single stranded nucleotide molecule (e.g., donor molecule) is at least partially complementary to the first single stranded nucleotide (e.g., acceptor molecule). When the acceptor molecule is hybridized to the donor molecule, the result is a hybrid molecule comprising the acceptor and donor molecule. The hybridized hybrid molecule can be ligated as and be subject to further manipulations.

Accordingly, the invention provides a ligation approach that is based on hybridization of two single stranded nucleotides, the first single stranded nucleotide is referred to as an acceptor molecule and the second single stranded nucleotide is referred to as a donor molecule. In some instances, the acceptor molecule can be of any sequence and the donor oligonucleotide can be of any sequence and comprises a hairpin structure.

In one embodiment, the invention includes compositions and methods for ligating single stranded nucleic acids wherein the ligation is based on hybridization of an acceptor molecule with a donor molecule that is fast, efficient, and has a low-sequence bias. In one embodiment, the structure of the donor molecule comprises a stem-loop intramolecular nucleotide base pairing (i.e., hairpin) and a 3'-overhang region such that the overhang is able to hybridize to nucleotides present in the 3' end of any acceptor molecule.

Acceptor

The acceptor molecule as well as the donor molecule of the invention comprises nucleic acids from any source. A nucleic acid in the context of the present invention includes but is not limited to deoxyribonucleic acid (DNA), ribonucleic acid (RNA) and peptide nucleic acid (PNA). DNA and RNA are naturally occurring in organisms, however, they may also exist outside living organisms or may be added to organisms. The nucleic acid may be of any origin, e.g., viral, bacterial, archae-bacterial, fungal, ribosomal, eukaryotic or prokaryotic. It may be nucleic acid from any biological sample and any organism, tissue, cell or sub-cellular compartment. It may be nucleic acid from any organism. The nucleic acid may be pre-treated before quantification, e.g., by isolation, purification or modification. Also artificial or synthetic nucleic acid may be used. The length of the nucleic acids may vary. The nucleic acids may be modified, e.g. may comprise one or more modified nucleobases or modified sugar moieties (e.g., comprising methoxy groups). The backbone of the nucleic acid may comprise one or more peptide bonds as in peptide nucleic acid (PNA). The nucleic acid may comprise a base analog such as non-purine or non-pyrimidine analog or nucleotide analog. It may also comprise additional attachments such as proteins, peptides and/or or amino acids.

Donor

In one embodiment, the donor molecule of the invention comprises a double stranded region and a single stranded region. In one embodiment, the single stranded region is found at the 3' end of the donor molecule. In one embodiment, the single stranded region is at least partially complementary to a sequence found on an acceptor molecule of the invention. This complementary sequence found in the donor molecule allows for the hybridization between the acceptor and donor molecules of the invention.

In one embodiment, the donor molecule is a single stranded oligonucleotide that forms an intramolecular stem structure, i.e., a hairpin structure. As used elsewhere herein, a stem structure encompasses a stem-loop structure. Preferably, the intramolecular stem structure produces a 3' overhang.

In one embodiment, the donor molecule of the invention comprises: (a) a 5' phosphate; (b) a stem or a stem-loop structure; and (c) a 3' overhang.

In one embodiment, the donor molecule of the invention is a chimeric molecule comprising nucleic acid that has a DNA 5'-end and an RNA 3'-end (or synthetic 3'-end). In another embodiment, the donor molecule comprises nucleic acid that has an RNA 5'-end and a DNA 3'-end.

3' Overhang

In one embodiment, the 3'-overhang region of the donor molecule comprises nucleotides that hybridize to nucleotides found in the 3' end of the acceptor molecule such that the hybridization between the acceptor molecule and the donor molecule forms a structure referred elsewhere herein as a hybrid molecule of the invention that can be ligated by either enzymatic or chemical means.

In one embodiment, the 3'-overhang region comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 20 nucleotides, at least 25 nucleotides, at least 30 nucleotides, at least 35 nucleotides, or at least 40 nucleotides that are complementary to sequences found in the acceptor molecule when the acceptor and donor molecules are hybridized to one another. In this manner, the 3'-overhang region of the donor molecule is considered as the region of the donor molecule that binds to the 3' region of the acceptor molecule.

In various embodiments, the 3'-overhang region comprises at least 1 nucleotide, preferably at least 2 nucleotides, preferably at least 3 nucleotides, preferably at least 4 nucleotides, and preferably at least 5 nucleotides that are mismatched with nucleotides found in the acceptor molecule when the acceptor and donor molecules are hybridized to one another.

In one embodiment, the hybridization between the acceptor molecule and the donor molecule forms a structure that comprises a "nick" wherein the nick can be ligated by either enzymatic or chemical means. A nick in a strand is a break in the phosphodiester bond between two nucleotides in the backbone in one of the strands of a duplex between a sense and an antisense strand.

In another embodiment, the hybridization between the acceptor molecule and the donor molecule forms a structure that comprises a "gap" wherein the gap can be ligated by either enzymatic or chemical means. A gap in a strand is a break between two nucleotides in the single strand.

In one embodiment, the hybridization between the acceptor molecule and the donor molecule forms a structure that is stable at temperatures that is as high as 35° C., as high as 40° C., as high as 45° C., as high as 50° C., as high as 55° C., as high as 60° C., as high as 65° C., as high as 70° C., as high as 75°, as high as 80° C., as high as 85° C., or more.

Stem

A donor molecule that is useful in the methods of the invention comprises a single-stranded oligonucleotide having a double-stranded portion formed of two self-complementary segments, optionally having a loop at one end, and a short overhanging single strand at the other. Thus, for purposes of the present invention, a hairpin may be defined as a double-helical region formed by nucleotide base-pairing between adjacent, inverted, at least partially complementary sequences in a single-stranded nucleic acid, preferably within the same single stranded nucleic acid.

The donor molecule is designed in a manner that the stem structure maintains its structure prior to and under conditions suitable for hybridization between the donor and acceptor molecules. In this manner, the nick or gap formed through the hybridization between the donor and acceptor molecules can be fixed by way of ligation. In some instances, the donor molecule is designed to also have the stem structure be retained under conditions where the nick or gap is ligated by either enzymatic or chemical means. In this situation, a hybrid molecule is created by the ligation between the acceptor and donor molecule wherein the hybrid molecule comprises a larger and more stable stem structure than was present in the donor alone.

In one embodiment, the intramolecular stem structure preferably maintains the stem structure under conditions suitable for hybridization between the donor and acceptor molecule. For example, the stem structure is designed to maintain its structure under conditions where the acceptor and donor molecule hybridize.

In some instances, the donor molecule is designed that in some conditions, the intramolecular stem structure has reduced stability where the stem structure is unfolded. In this manner, the stem structure can be designed so that the stem structure can be relieved of its intramolecular base pairing and resemble more of a linear molecule. In one embodiment, the donor molecule is designed where the relief of the intramolecular stem structure is thermodynamically favored over the intramolecular stem structure. For example, following the generation of a hybrid molecule of the invention that comprises a stem structure, it is often desirable to amplify or sequence at least a portion of the sequence present in the acceptor molecule portion of the hybrid molecule of the invention. This can be accomplished by thermodynamically relieving the intramolecular stem structure present in the hybrid molecule by raising the temperature or adding a chemical denaturant. Once the intramolecular stem structure is relieved, a probe or primer can be used to sequence or amplify at least a portion of the sequence present in the acceptor molecule.

As discussed elsewhere herein, the stem is designed to form a stable structure during hybridization and ligation between the acceptor and donor molecule, yet flexible enough that the stem can be relieved under conditions for amplification or sequencing.

In accordance with the present invention, there are provided predetermined stem oligonucleotide sequences containing stretches of complementary sequences that form the stem structure. In one embodiment, the stem can comprise at least 3 nucleotide pairs, at least 4 nucleotide pairs, at least 5 nucleotide pairs, at least 6 nucleotide pairs, at least 7 nucleotide pairs, at least 8 nucleotide pairs, at least 9 nucleotide pairs, at least 10 nucleotide pairs, at least 11 nucleotide pairs, at least 12 nucleotide pairs, at least 13 nucleotide pairs, at least 14 nucleotide pairs, at least 15 nucleotide pairs, at least 20 nucleotide pairs, at least 25 nucleotide pairs, at least 30 nucleotide pairs, at least 35 nucleotide pairs, at least 40 nucleotide pairs, at least 45 nucleotide pairs, at least 50 nucleotide pairs, at least 55 nucleotide pairs, at least 60 nucleotide pairs, at least 65 nucleotide pairs, at least 70 nucleotide pairs, at least 75 nucleotide pairs, such that these complementary stretches anneal to provide a donor stem oligonucleotide.

In one embodiment, the stem region comprises at least 1 mismatched pair, at least 2 mismatched pairs, at least 3 mismatched pairs, at least 4 mismatched pairs, at least 5 mismatched pairs, at least 5 mismatched pairs, at least 6 mismatched pairs, at least 7 mismatched pairs, at least 8 mismatched pairs, at least 9 mismatched pairs, at least 10 mismatched pairs, at least 11 mismatched pairs, at least 12 mismatched pairs, at least 13 mismatched pairs, at least 14 mismatched pairs, at least 15 mismatched pairs, at least 20 mismatched pairs, at least 25 mismatched pairs, at least 30 mismatched pairs, at least 35 mismatched pairs, at least 40 mismatched pairs, at least 45 mismatched pairs, or at least 50 mismatched pairs.

In one embodiment, it is desirable to have a sufficient amount of mismatch pairs so that the structure of the stem is unstable at a high temperature of at least 60° C., at least 65° C., at least 70° C., at least 75° C., at least 80° C., at least 85° C., at least 90° C., at least 95° C., at least 96°, at least 97° C., at least 98° C., or at least 99° C.

In some instances, the donor molecule of the invention comprises a stem-loop structure. The loop can comprise any number of nucleotides. In one embodiment, the loop structure comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 20 nucleotides, at least 25 nucleotides, at least 30 nucleotides, at least 35 nucleotides, or at least 40 nucleotides. Preferably, the loop comprises about 2-30 nucleotides.

Engineered Features

In one embodiment, the donor molecule of the invention is designed to comprise a primer binding site. The primer binding site can be designed to be in any, or more than one, region of the donor molecule. In some instances, it is useful that at least part of the primer binding site be in the loop. This is because base pairs between the primer and loop do not have to compete with base pairs within the stem.

In general, the sequence of the primer binding site can be designed such that the sequence thereof is more complementary to a corresponding primer compared to to any other portion of the acceptor, donor, or hybrid molecules of the invention. The primer binding site can be any length that supports specific and stable hybridization between the primer binding site and a primer. For this purpose, a length of about 10 to about 35 nucleotides is preferred, with a primer binding site of about 16 to about 20 nucleotides long being most preferred.

As discussed elsewhere herein, the stem is designed to form a stable structure during hybridization and ligation between the acceptor and donor molecule, yet flexible enough that the stem can be relieved or otherwise unfold under conditions for amplification or sequencing.

Therefore, in some instances, it is desirable to design the donor molecule to have the stem structure be unfolded under suitable conditions for amplification (e.g., suitable denaturing temperatures). For example, following the formation of a ligated hybrid molecule comprising a donor and acceptor molecule of the invention, it is desirable to remove the stem structure and thereby create a more linear structure so that a primer can bind to the corresponding primer binding site. For this purpose, it is preferred that the intramolecular stem structure or stem loop structure be less stable in conditions where it is desirable for a primer to bind to its corresponding primer binding site (or, put another way, the hybrid between a primer and a primer binding site should be more stable than the reformation of the intramolecular stem structure or stem loop structure). For example, when conditions that promote the hybrid molecule of the invention comprising a stem structure to lose its intramolecular base pairing and favor a more unfolded structure, it is desirable to have the hybridization between the primer and the primer binding site be more stable than the hybridization between the intramolecular bases within the stem structure of the hybrid molecule. In this way, the primer can bind to the primer binding site before the stem structure can be reformed in the hybrid molecule.

In another embodiment, once the intramolecular stem structure is relieved or otherwise is unfolded to resemble an unfolded structure, a probe or primer can be used to sequence or amplify at least a portion of the sequence present in the acceptor portion of the hybrid molecule of the invention.

In another, the donor molecule of the invention is designed to comprise a restriction site. The restriction site can be designed to be in any, or more than one, region of the donor molecule or the hybrid product resulting from ligation. Treatment with the corresponding restriction enzyme can result in the cleavage of the molecule at those residues corresponding to the restriction enzyme site. The resulting product following restriction enzyme cut can then be manipulated in downstream reactions, such as for example in cloning, sequencing, or otherwise inserting the product into a desired plasmid.

In another, the donor molecule of the invention is designed to comprise a label, for example a tag sequence. The tag sequence can be designed to be in any, or more than one, region of the donor molecule. A tag sequence that is present in the donor molecule is designed so as not to substantially impair or interfere with the ability of the donor molecule to hybridize with the acceptor molecule. Moreover, the tag sequence will be of sufficient length and composition such that once the tag sequence has been incorporated into the donor molecule or hybrid molecule of the invention (e.g., molecule comprising both the acceptor and donor molecule), a tag-specific priming oligonucleotide complementary to the tag can then be used to participate in subsequent manipulation. Skilled artisans will recognize that the design of tag sequences and tagged oligonucleotides for use in the present invention can follow any of a number of suitable strategies, while still achieving the objectives and advantages described herein.

In some instances, the tag sequence includes at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these.

In other instances, the ligation could be used for sequencing single molecules of DNA. If the donor molecule is covalently attached to a solid support, then the acceptor molecule of unknown sequence could anneal to its templating region and then DNA ligase could be used to seal the nick between the donor and acceptor. The acceptor could then be sequenced by next generation sequencing methods.

In yet other instances, the ligation could be used for library preparation procedures or yet to be identified molecular biology procedures that benefit from a fast, efficient, and low-sequence bias. An example of a library preparation method where the present invention is applicable can be found in Meyer et al. (2012 Science 338 (6104):222-6)).

Methods

This invention relates to ligating single stranded nucleic acids. In one embodiment, the method comprises: a) contacting a single stranded acceptor nucleic acid molecule with a donor nucleic acid molecule wherein the donor nucleic acid molecule comprises one or more nucleic acids having a double stranded region and a single stranded 3' terminal region; b) hybridizing the single stranded 3' terminal region of the donor nucleic acid molecule to the acceptor molecule thereby forming an acceptor-donor hybrid molecule comprising a nick or gap between the acceptor nucleic acid and donor nucleic acid molecule; c) and ligating one 5' end of the donor nucleic acid molecule to the 3' end of the acceptor nucleic acid molecule.

In one embodiment, the hybridization between the acceptor molecule and the donor molecule forms a structure that comprises a nick or gap wherein the nick or gap can be filled and/or ligated by either enzymatic or chemical means.

"Ligation" refers to the joining of a 5'-phosphorylated end of one nucleic acid molecule to a 3'-hydroxyl end of the same or another nucleic acid molecule by an enzyme called a "ligase." Alternatively, in some embodiments of the invention, ligation is effected by a type I topoisomerase moiety attached to one end of a nucleic acid (see U.S. Pat. No. 5,766,891, incorporated herein by reference). The terms "ligating," "ligation," and "ligase" are often used in a general sense herein and are meant to comprise any suitable method and composition for joining a 5'-end of one nucleic acid to a 3'-end of the same or another nucleic acid.

In addition, ligation can be mediated by chemical agents. Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in, among other places, Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowski, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); and U.S. Pat. No. 5,476,930.

In general, if a nucleic acid to be ligated comprises RNA, a ligase such as, but not limited to, T4 RNA ligase, a ribozyme or deoxyribozyme ligase, Tsc RNA Ligase (Prokaria Ltd., Reykjavik, Iceland), or another ligase can be used for non-homologous joining of the ends. T4 DNA ligase can be used to ligate DNA molecules, and can also be used to ligate RNA molecules when a 5'-phosphoryl end is adjacent to a 3'-hydroxyl end annealed to a complementary sequence (e.g., see U.S. Pat. No. 5,807,674 of Tyagi).

If the nucleic acids to be joined comprise DNA and the 5'-phosphorylated and the 3'-hydroxyl ends are ligated when the ends are annealed to a complementary DNA so that the ends are adjacent (such as, when a "ligation splint" is used), then enzymes such as, but not limited to, T4 DNA ligase, Ampligase™. DNA Ligase (Epicentre Technologies, Madison, Wis. USA), Tth DNA ligase, Tfl DNA ligase, or Tsc DNA Ligase (Prokaria Ltd., Reykjavik, Iceland) can be used. However, the invention is not limited to the use of a particular ligase and any suitable ligase can be used. Still further, Faruqui discloses in U.S. Pat. No. 6,368,801 that T4 RNA ligase can efficiently ligate DNA ends of nucleic acids that are adjacent to each other when hybridized to an RNA strand. Thus, T4 RNA ligase is a suitable ligase of the invention in embodiments in which DNA ends are ligated on a ligation splint oligonucleotide comprising RNA or modified RNA, such as, but not limited to modified RNA that contains 2'-F-dCTP and 2'-F-dUTP made using the DuraScribe™ T7 Transcription Kit (Epicentre Technologies, Madison, Wis. USA) or the N4 mini-vRNAP Y678F mutant enzyme described herein. With respect to ligation on a homologous ligation template, especially ligation using a "ligation splint" or a "ligation splint oligonucleotide" (as discussed elsewhere herein), a region, portion, or sequence that is "adjacent" to another sequence directly abuts that region, portion, or sequence.

In some embodiments, a gap of at least one nucleotide is present in the unligated hybrid molecule of the invention that comprises a donor molecule and an acceptor molecule. In some embodiments, the gap is filled in by a polymerase, and the resulting product ligated. Several modifying enzymes are utilized for the nick repair step, including but not limited to polymerases, ligases, and kinases. DNA polymerases that can be used in the methods of the invention include, for example, E. coli DNA polymerase I, Thermoanaerobacter thermohydrosulfuricus polymerase I, and bacteriophage phi 29. In a preferred embodiment, the ligase is T4 DNA ligase and the kinase is T4 polynucleotide kinase.

In one embodiment, ligation of the donor and acceptor molecule involves contacting the hybridized molecules with a ligase under conditions that allow for ligation between any two terminal regions of the molecules whose 3' and 5' ends after hybridization are positioned in a way that ligation may occur.

Any DNA ligase is suitable for use in the ligation step. Preferred ligases are those that preferentially form phosphodiester bonds at nicks in double-stranded DNA. That is, ligases that fail to ligate the free ends of free single-stranded DNA at a significant rate are preferred. In some instances, thermostable ligases can be used. In other instances, thermosensitive ligases are preferred because the ligase can be heat inactivated. Many suitable ligases are known, such as T4 DNA ligase (Davis et al., Advanced Bacterial Genetics—A Manual for Genetic Engineering (Cold Spring Harbor Laboratory, Cold Spring Harbor, N.Y., 1980)), E. coli DNA ligase (Panasnko et al., J. Biol. Chem. 253:4590-4592 (1978)), AlVlPLIGASE™ (Kalin et al., Mutat. Res., 283(2): 119-123 (1992); Winn-Deen et al., Mol Cell Probes (England) 7(3):179-186 (1993)), Taq DNA ligase (Barany, Proc. Natl. Acad. Sci. USA 88:189-193 (1991), Thermus thermophilus DNA ligase (Abbott Laboratories), Thermus scotoductus DNA ligase and Rhodothernius marinus DNA ligase (Thorbjarnardottir et al., Gene 151:177-180 (1995)). T4 DNA ligase is preferred for ligations involving RNA target sequences due to its ability to ligate DNA ends involved in DNA:RNA hybrids (Hsuih et al., Quantitative detection of HCV RNA using novel ligation-dependent polymerase chain reaction, American Association for the Study of Liver Diseases (Chicago, Ill., Nov. 3-7, 1995)).

Amplification

The ligation product that comprises the donor and acceptor molecule can be isolated or amplified using a primer that corresponds to a primer binding site present in the ligated product (i.e., primer binding site present in the donor molecule or the resulting hybrid product).

In particular embodiments of the invention the quantifying steps comprise a method selected from the group consisting of gel electrophoresis, capillary electrophoresis, labelling reactions with subsequent detection measures and quantitative real-time PCR or isothermal target amplification. Preferably, the quantification steps comprise quantitative real-time PCR or quantitative real-time isothermal amplification. More preferably, quantification comprises quantitative real-time PCR.

The ligation product or otherwise the template nucleic acid may be amplified, while attached or unattached to beads, by any suitable method of amplification including transcription-based amplification systems (Kwoh D. et al., Proc. Natl. Acad. Sci. (U.S.A.) 86:1173 (1989); Gingeras T. R. et al., WO 88/10315; Davey, C. et al., EP Publication No. 329,822; Miller, H. I. et al., WO 89/06700), "RACE" (Frohman, M. A., In: PCR Protocols: A Guide to Methods and Applications, Academic Press, NY (1990)) and one-sided PCR (Ohara, O. et al., Proc. Natl. Acad. Sci. (U.S.A.) 86.5673-5677 (1989)). Still other methods such as di-oligonucleotide amplification, isothermal amplification (Walker, G. T. et al., Proc. Natl. Acad. Sci. (U.S.A.) 89:392-396 (1992)), Nucleic Acid Sequence Based Amplification (NASBA; see, e.g., Deiman B et al., 2002, Mol. Biotechnol. 20(2):163-79), whole-genome amplification (see, e.g., Hawkins T L et al., 2002, Curr Opin Biotechnol. 13(1):65-7), strand-displacement amplification (see, e.g., Andras S C, 2001, Mol. Biotechnol. 19(1):29-44), rolling circle amplification (reviewed in U.S. Pat. No. 5,714,320), and other well-known techniques may be used in accordance with the present invention. In certain aspects, a nucleic acid template is amplified after encapsulation with a bead in a microreactor. Alternatively, a nucleic acid template is amplified after distribution onto a multiwell surface, e.g., a PicoTiter plate.

In a preferred embodiment, DNA amplification is performed by PCR. PCR according to the present invention may be performed by contacting the target nucleic acid with a PCR solution comprising all the necessary reagents for PCR. Then, PCR may be accomplished by exposing the mixture to any suitable thermocycling regimen known in the art. In a preferred embodiment, 30 to 50 cycles, preferably about 40 cycles, of amplification are performed. It is desirable, but not necessary, that following the amplification procedure there be one or more hybridization and extension cycles following the cycles of amplification. In a preferred embodiment, 10 to 30 cycles, preferably about 25 cycles, of hybridization and extension are performed (e.g., as described in the examples). Routinely, the template DNA is amplified until typically at least 10,000 to 50,000,000 copies are immobilized on each bead. It is recognized that for nucleic acid detection applications, fewer copies of template are required. For nucleic acid sequencing applications we prefer that at least two million to fifty million copies, preferably about ten million to thirty million copies of the template DNA are immobilized on each bead. The skilled artisan will recognize that the size of bead (and capture site thereon) determines how many captive primers can be bound (and thus how many amplified templates may be captured onto each bead).

In particular embodiments of the invention the polymerase used for quantitative real-time PCR is a polymerase from a thermophile organism or a thermostable polymerase or is selected from the group consisting of *Thermus thermophilus* (Tth) DNA polymerase, *Thermus aquaticus* (Taq) DNA polymerase, *Thermotoga maritima* (Tma) DNA polymerase, *Thermococcus litoralis* (Tli) DNA polymerase, *Pyrococcus furiosus* (Pfu) DNA polymerase, *Pyrococcus woesei* (Pwo) DNA polymerase, *Pyrococcus kodakaraensis* KOD DNA polymerase, *Thermus filiformis* (Tfi) DNA polymerase, *Sulfolobus solfataricus* Dpo4 DNA polymerase, *Thermus pacificus* (Tpac) DNA polymerase, *Thermus eggertssonii* (Teg) DNA polymerase, *Thermus brockianus* (Tbr) and *Thermus flavus* (Tfl) DNA polymerase.

In preferred embodiments of the invention the primer or probe is labelled with one or more fluorescent dye(s) and/or quencher(s) and wherein the quantifying steps comprise detecting fluorescence signals in the sample.

Particularly, the fluorescently labelled primers or probes are labelled with a dye selected from the group consisting of FAM, VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor and PET or analogous dyes with similar excitation and emission properties.

In one embodiment, the primer or probe is a LightCycler probe (Roche) or the hydrolysis probe is a TaqMan probe (Roche). In other embodiments the primer or probe includes but is not limited to molecular beacon, Scorpion primer, Sunrise primer, LUX primer and Amplifluor primer.

Applications

The ssDNA ligation composition and method of the present invention may be used in a wide variety of protocols and technologies. For example, in certain embodiments, ssDNA ligation is used in the fields of molecular biology, genomics, transcriptomics, epigenetics, nucleic acid sequencing, and the like. That is, ssDNA ligation may be used in any technology that may require or benefit from the ligation of ssDNA. Exemplary technologies, include, but are not limited to Ligation-Mediated PCR (LMPCR); cDNA library construction; DNA epigenome (such as m5C) and RNA methylome (such as m6A) assays, high-throughput next generation sequencing technologies including but not limited to Illumina, SOLiD, and Ion Torrent sequencing; and single nucleic acid molecule real time sequencing (SMRT) including, but not limited to, technologies from Pacific Bioscience and Oxford Nanopore Technologies such as zero-mode waveguide or nanopore sequencing, respectively.

In one embodiment, the ssDNA ligation composition and method of the invention is applicable to DMS/SHAPE-LMPCR and Structure-Seq, and DMS-seq. These technologies are described, for example, in Kwok et al. (Kwok et al, 2013, Nature Communications, 4: article number: 297), Ding et al. (Ding et al., 2013, Nature, November 24. doi: 10.1038/nature12756), and Rouskin et al. (Rouskin et al., 2013, Nature, doi:10.1038/nature12894), respectively, the contents of which are incorporated by reference herein in their entirety.

In one embodiment, the ssDNA ligation composition and method of the invention can be used in a DMS/SHAPE-LMPCR method to determine RNA structure in vivo and in vitro in low-abundance transcripts, for any organism or tissue.

In another embodiment, the ssDNA ligation composition and method of the invention can be used in Structure-Seq, a method that allows for genome-wide profiling of RNA secondary structure, both in vivo and in vitro, for any organism or tissue.

In another embodiment, the ssDNA ligation composition and method of the invention can be used in DMS-Seq, another method that allows genome-wide probing of RNA secondary structure, both in vivo and in vitro, in any organism or tissue.

Kits

The present invention also relates to a kit for performing any of the above described methods, wherein the kit comprises one or more of: (a) a donor molecule; (b) a ligase; and, optionally, (c) a primer substantially complementary to a primer binding site present in the donor molecule In one embodiment, the kit additionally comprises a ligase. In another embodiment, the kit additionally comprises a polymerase. The kit may additionally also comprise a nucleotide mixture and (a) reaction buffer(s) and/or a set of primers and optionally a probe for the amplification and detection of the ligation product between an acceptor and donor molecule.

In particular embodiments, the kit additionally comprises one or more pre-quantified calibrator nucleic acids, a set of primers for the amplification of said calibrator nucleic acids and a first nucleic acid probe substantially complementary to a sequence on said pre-quantified nucleic acid.

In some embodiments, one or more of the components are premixed in the same reaction container.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: A Hybridization-Based Approach for Quantitative and Low-Bias Single-Stranded DNA Ligation Single-stranded (ss) DNA ligation is a crucial step in many biochemical assays. Efficient ways of carrying out this reaction are lacking, however. As demonstrated herein, existing ssDNA ligation methods suffer from slow kinetics, poor yield, and severe nucleotide preference. To resolve these issues, a hybridization-based strategy is presented herein, which provides efficient and low-bias ligation of ssDNA. The ligation approach presented herein is based on hybridization of an incoming acceptor DNA oligonucleotide to a hairpin DNA using T4 DNA ligase, which is fast, efficient, low-bias, and integrates seamlessly with downstream protocols. This technique can be applied in protocols that require ligation of ssDNA, including Ligation-Mediated PCR (LMPCR), and cDNA library construction. The technique could also be used in a variety of high-throughput, next generation sequencing technologies including, but not limited to, Illumina, SOLiD, and Ion Torrent sequencing as well as the sequencing of single molecules of DNA including, but not limited to, technologies from Pacific Bioscience such as SMRT.

The materials and methods employed in these experiments are now described.

DNA Oligonucleotides and Purification

All PAGE-purified 24 nucleotide Cy5-labeled acceptor DNA were purchased from Sigma Aldrich. All remaining DNAs were from Integrated DNA Technologies (IDT). All donor oligonucleotides were purified by 10% urea-polyacrylamide gel electrophoresis, and the bands were excised individually under UV shadowing, which was brief in order to prevent formation of photolesions (Kladwang et al., 2012, Sci. Rep. 2:517). Each band was crushed and soaked in 10 mM Tris, pH 7.5, 1 mM EDTA, 250 mM NaCl (1×TEN$_{250}$) overnight at room temperature with constant rotary shaking. The gel mixture was filtered against a 0.25 μm filter, subjected to ethanol precipitation by addition of 3× volume of 100% ethanol, and frozen in dry ice for an hour. The frozen slurry was subsequently centrifuged at 13,000 rpm for 20 min, and the pellet washed with cold 70% ethanol to remove residual salts. Residual ethanol was removed by speed-vac for 5-10 min, and the pellet was dissolved in water and quantified with UV-spectroscopy to determine the DNA concentration. DNAs were stored at −20° C. both before and after experiments, and the vials containing the Cy5 and FAM labeled acceptor DNAs were wrapped with aluminum foil to prevent photobleaching, and stored at −20° C. both before and after use.

Ligation Reaction and Data Collection

Figure 7:
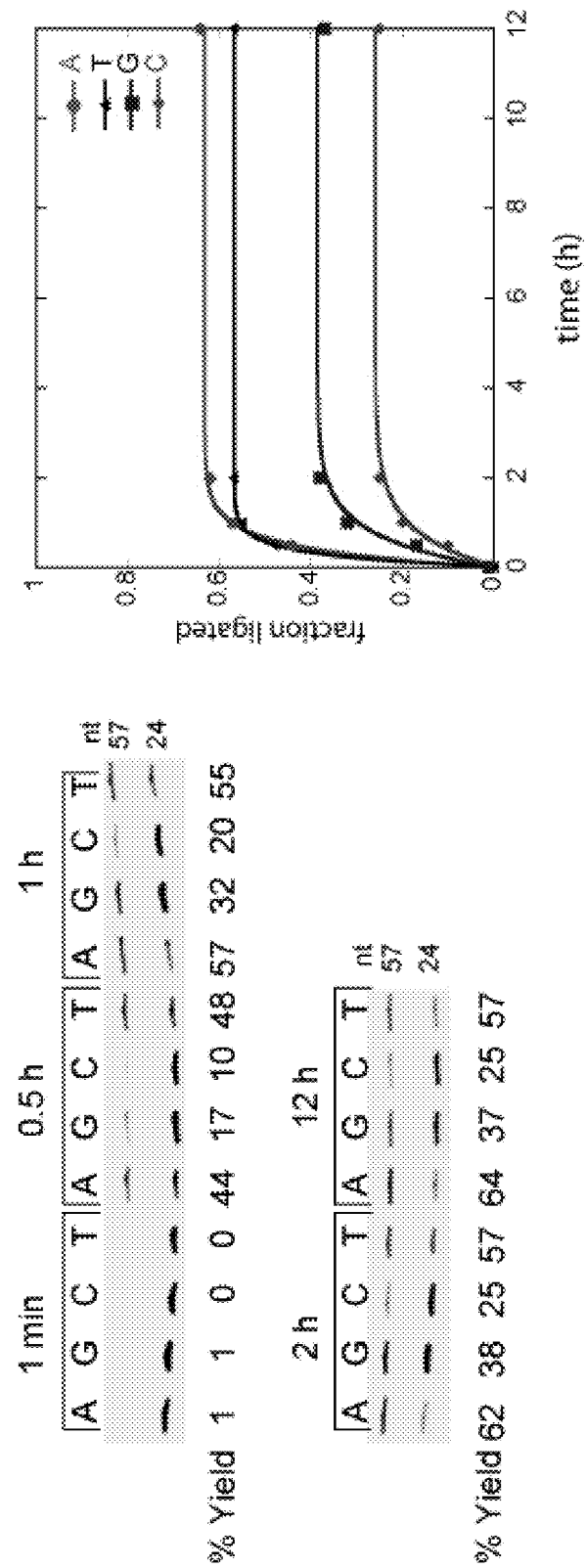
FIG. 7 is a set of images depicting the results of experiments examining the ssDNA ligation kinetics and nucleotide preference of wild-type (WT; 33 mer) donor oligonucleotide using Circligase I. The reaction contained 100 pmol of 5'p donor, 1 pmol of Cy5-labelled acceptor, 20% PEG 8000, 50 mM MOPS (pH 7.5), 10 mM KCl, 5 mM $MgCl_2$, 1 mM DTT, 0.05 mM ATP, 2.5 mM $MnCl_2$ and 200 U Circligase I. Reaction was performed at 68° C. and time points were taken at indicated time intervals.
Figure 8:
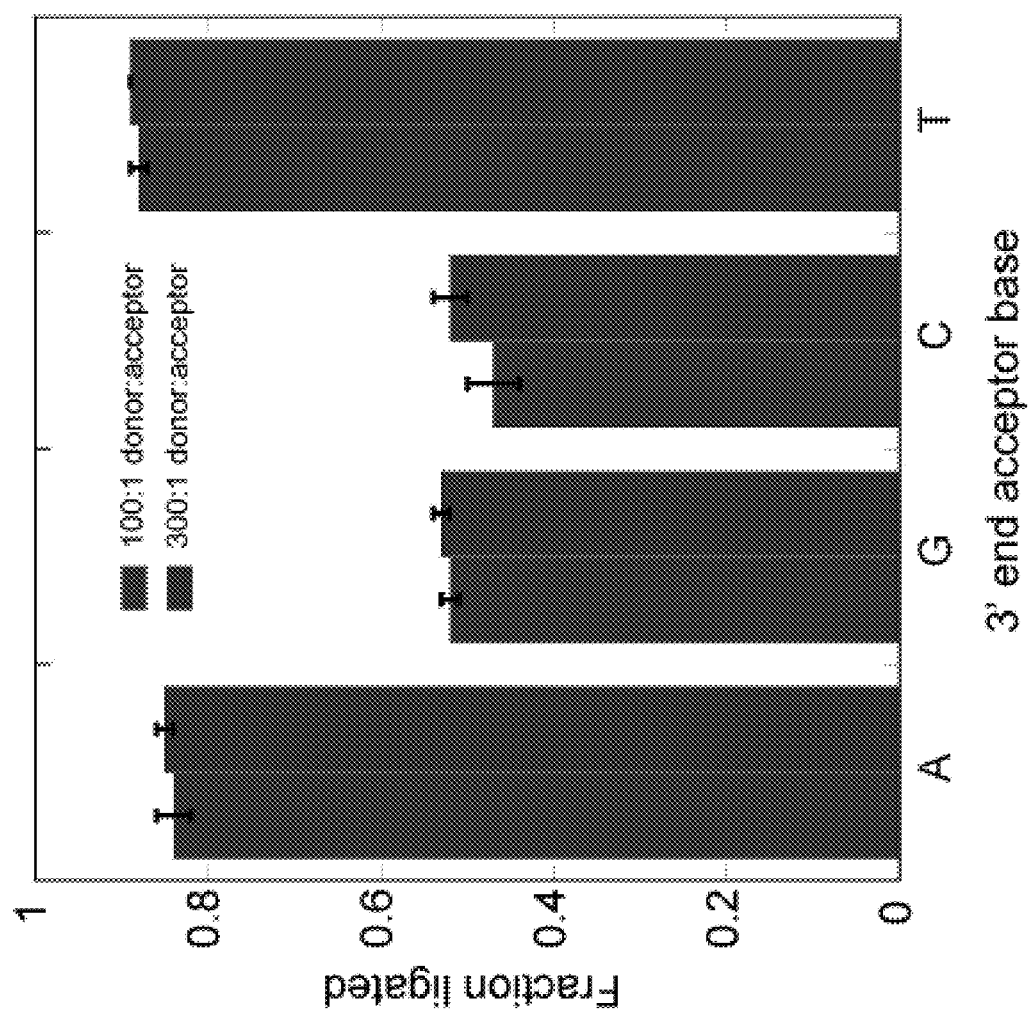
FIG. 8 is a graph depicting the results of a nucleotide preference test of donor oligonucleotide 3 under different donor:acceptor ratios using Circligase I. The reaction contained 100 or 300 pmol of 5'p donor, 1 pmol of Cy5-labelled acceptor, 50 mM MOPS (pH 7.5), 10 mM KCl, 5 mM $MgCl_2$, 1 mM DTT, 0.05 mM ATP, 2.5 mM $MnCl_2$ and 200 U Circligase I. Reaction was performed at 65° C. for 12 h, and then 85° C. for 15 min to deactivate the enzyme. The fraction ligated shown is the average value of 3 trials and the error bar is standard deviation. Note that increasing 3× in donor:acceptor ratio did not alter the fraction ligated significantly, indicating that the donor:acceptor ratio is saturating at 100:1 ratio.
Figure 9:
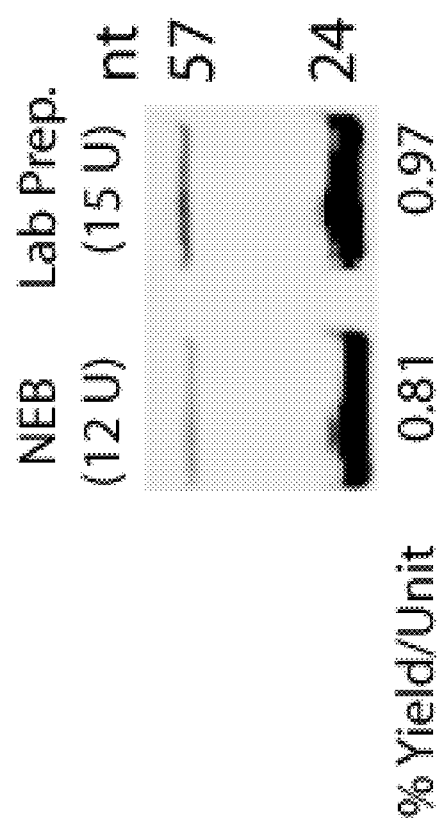
FIG. 9 is an image depicting the results of ssDNA ligation of WT donor and "G" acceptor using either New England Biolabs (NEB) or a laboratory preparation of T4 DNA ligase. 12 U of NEB T4 DNA ligase and 15 U of laboratory preparation T4 DNA ligase were used, and the ligation reaction contained 100 pmol of 5'p donor, 1 pmol of Cy5-labelled acceptor, 50 mM Tris-HCl (pH 7.5), 10 mM $MgCl_2$, 10 mM DTT, and 1 mM ATP. Reaction was performed at 16° C. for 12 h. Results are quantified in "% yield/unit" to allow comparison between these two ligases.
Figure 10:
FIG. 10 is an image depicting the results of ssDNA ligation control experiments of WT donor and "G" acceptor using T4 DNA ligase. Individual components were omitted from the standard ligation reaction as indicated. The reaction was performed at 16° C. for 12 h. 'NA'=not applicable as no fluorophore was present.
Figure 11:
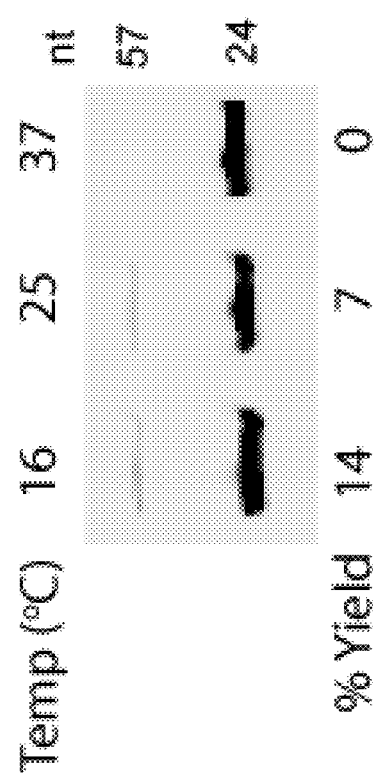
FIG. 11 is an image depicting the results of ssDNA ligation of WT donor and "G" acceptor under different temperatures using T4 DNA ligase. The standard ligation reaction containing 100 pmol of 5'p donor, 1 pmol of Cy5-labelled acceptor, 50 mM Tris-HCl (pH 7.5), 10 mM $MgCl_2$, 10 mM DTT, 1 mM ATP, 15 U laboratory preparation of T4 DNA ligase was incubated for 12 h at different temperatures as indicated.
Figure 12:
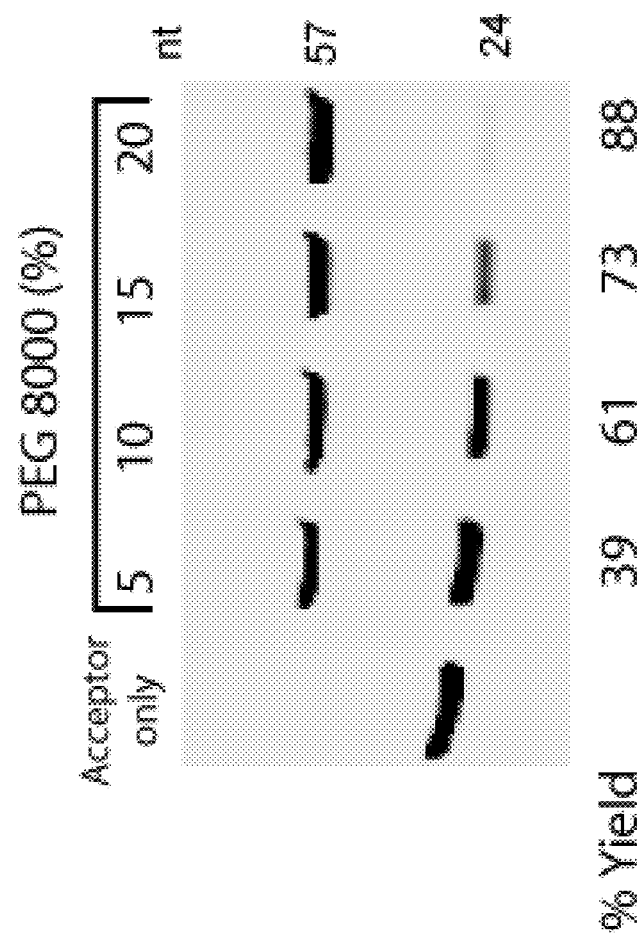
FIG. 12 is an image depicting the results of ssDNA ligation of WT donor and "G" acceptor under different PEG 8000 concentrations using T4 DNA ligase. The standard ligation reaction containing 100 pmol of 5'p donor, 1 pmol of Cy5-labelled acceptor, 50 mM Tris-HCl (pH 7.5), 10 mM $MgCl^2$, 10 mM DTT, 1 mM ATP, 15 U laboratory preparation of T4 DNA ligase was incubated for 12 h at 16° C. PEG 8000 concentration was varied as indicated.
Figure 13:
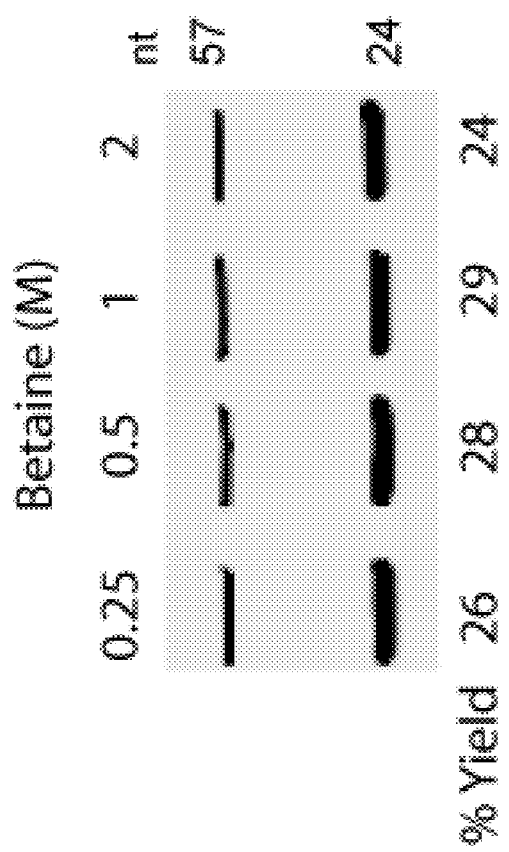
FIG. 13 is an image depicting the results of ssDNA ligation of WT donor and "G" acceptor under different betaine concentrations using T4 DNA ligase. The standard ligation reaction containing 100 pmol of 5'p donor, 1 pmol of Cy5-labelled acceptor, 50 mM Tris-HCl (pH 7.5), 10 mM $MgCl_2$, 10 mM DTT, 1 mM ATP, 15 U laboratory preparation of T4 DNA ligase was incubated for 12 h at 16° C. Betaine concentration was varied as indicated. The choice of 0.5 M betaine for optimized reaction was based on the bell-shape response observed here.
Figure 14:
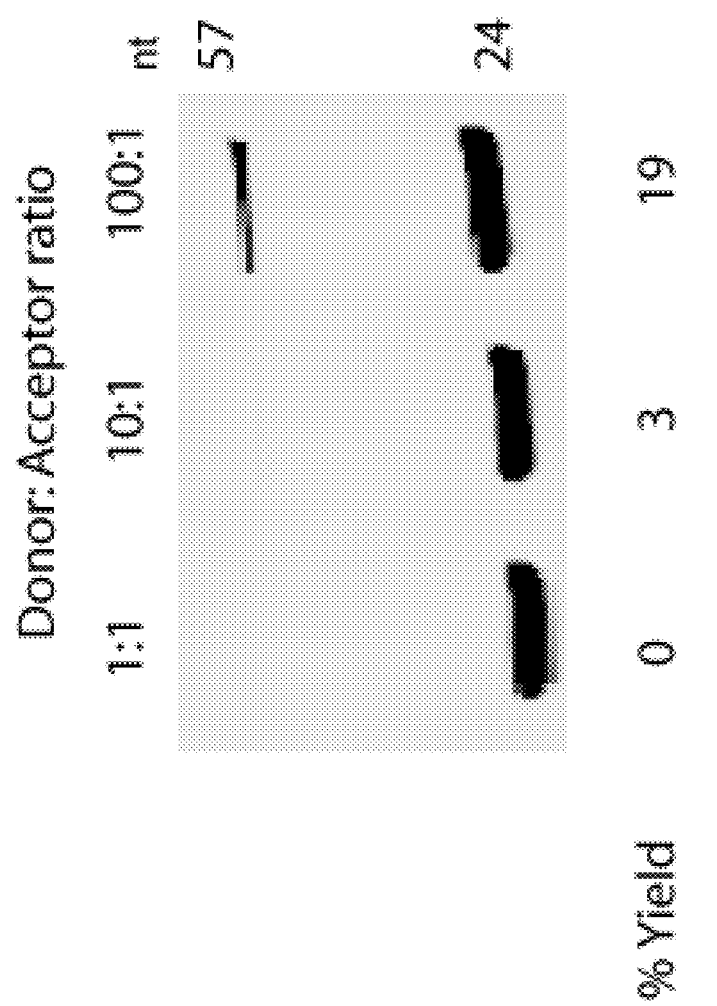
FIG. 14 is an image depicting the results of ssDNA ligation kinetics of WT donor and "G" acceptor under different donor:acceptor ratios using T4 DNA ligase. The standard ligation reaction containing different ratios of 5'p donor and Cy5-labelled acceptor as indicated, 50 mM Tris-HCl (pH 7.5), 10 mM $MgCl_2$, 10 mM DTT, 1 mM ATP, 15 U laboratory preparation of T4 DNA ligase was incubated for 12 h at 16° C.
Figure 15:
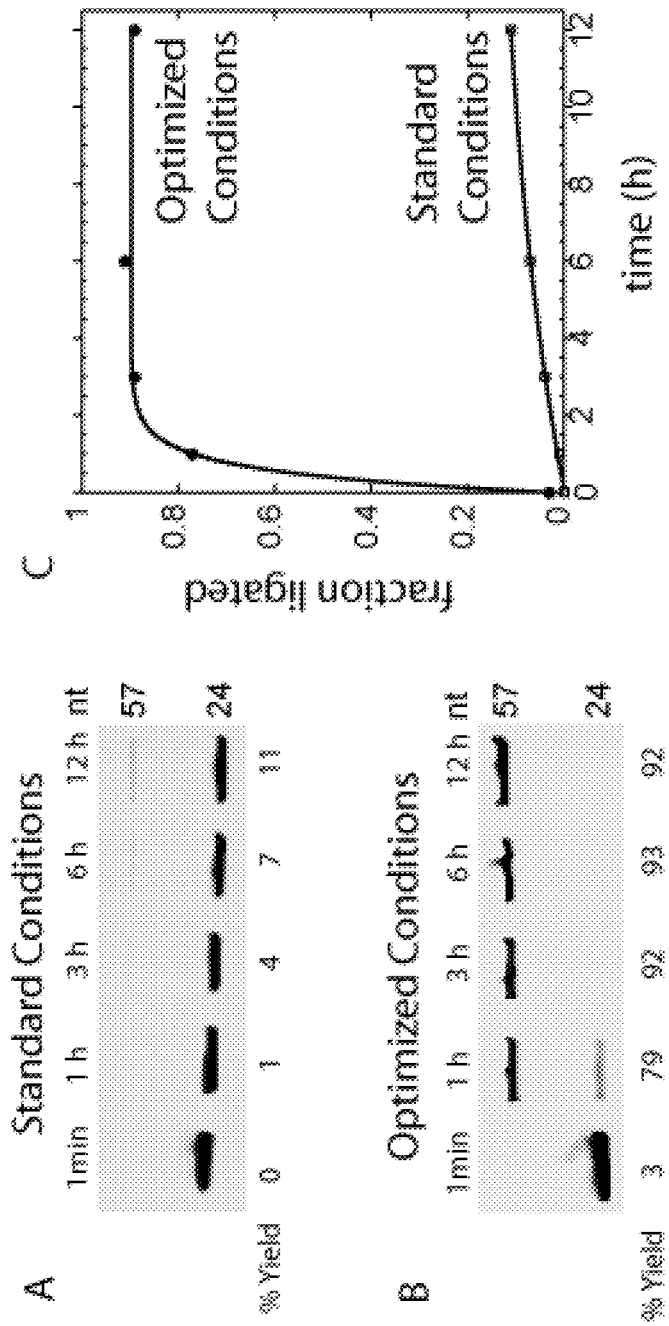
FIG. 15, comprising

Circligase I:

The reaction contained 100 pmol of 5'p donor, 1 pmol of Cy5-labelled acceptor, 50 mM MOPS (pH 7.5), 10 mM KCl, 5 mM MgCl$_2$, 1 mM DTT, 0.05 mM ATP, 2.5 mM MnCl$_2$ and 200 U Circligase I. The reaction was performed at 65° C. for 12 h, and then 85° C. for 15 min to deactivate the enzyme. In FIG. 7, 68° C. was used instead, and 20% PEG 8000 was included.

T4 RNA Ligase I:

The reaction contained 100 pmol of 5'p donor, 1 pmol of Cy5-labelled acceptor, 50 mM Tris-HCl (pH 7.5), 10 mM MgCl$_2$, 1 mM ATP, 1 mM DTT, and 20 U T4 RNA ligase I. The reaction was performed at 37° C. for 12 h, and then 65° C. for 15 min to deactivate the enzyme.

T4 DNA Ligase:

The ligation reaction contained 100 pmol of 5'p donor, 1 pmol of Cy5/FAM-labelled acceptor, 50 mM Tris-HCl (pH 7.5), 10 mM MgCl$_2$, 10 mM DTT, 1 mM ATP, and 15 U T4 DNA ligase. Ligation factors such as PEG 8000, betaine, temperature, and time were tested as described elsewhere herein (FIGS. 9-15). The reaction was performed at 16° C. for 12 h, and then 65° C. for 15 min to deactivate the enzyme. Unless otherwise indicated, a laboratory preparation of T4 DNA ligase was used.

All ligation reactions were quenched by 2× formamide dye with 20 mM EDTA. Samples were heated at 95° C. for 1.5 min, and 3 μl was loaded to an 8.3 M urea 10% polyacrylamide gel. The pre-heated gel (surface temperature at ~50-60° C.) was subjected to electrophoresis at 900-1000 V (constant) for 10-15 min, and then was directly scanned using the red laser (633 nm) of a Typhoon PhosphorImager 9410 and a 670 nm emission filter (BP 30 nm). The plate focus was set at 3 mm.

Data Processing and Analysis

The background corrected unligated (U) and ligated (L) bands were quantified using ImageQuant 5.2, and the ligation efficiency was calculated based on band intensities using the following equation:

$$\text{Ligation efficiency}=L/(U+L) \quad \text{(Equation 1)}.$$

The plots of fraction ligated versus time were fit to a single exponential equation in KaleidaGraph 3.5. The equation is as follows:

$$\text{Fraction ligated}=A+Be^{(-k_{obs}(t))} \quad \text{(Equation 2)},$$

where $k_{obs}$ is the observed first-order rate constant for ligation for the non-burst phase, t is time, A is the fraction of ligated product at completion, −B is the amplitude of the observable phase, 1−A is the unreactive fraction, and A+B is the burst fraction (Chadalavada et al., 2010, Biochemistry 49:5321-5330).

The results of the experiments are now described.

ssDNA Ligation Using Circligase I and T4 RNA Ligase I

To assay for ligation, two ssDNA oligonucleotides were designed, referred to as "acceptor" and "donor" (FIG. 1A). The acceptor oligonucleotide contains a Cy5 fluorophore at its 5'-terminus and a hydroxyl group at its 3'-terminus, whereas the donor oligonucleotide has a phosphate at its 5'-end and a C3-spacer group at its 3'-end that prevents donor self-oligomerization. For convenience of this ligation assay, these acceptor and donor oligonucleotides are relatively small, at 24 and 33 nucleotides, respectively, although any size is possible, as shown later. The Mfold-predicted secondary structures (Zuker, 2003, Nucleic Acids Res. 31:3406-3415) and the sequences of the initial acceptor and donor oligonucleotides are provided in FIG. 1A, and their importance for ssDNA ligation is tested below.

Figures 1B, 1C, 1D:
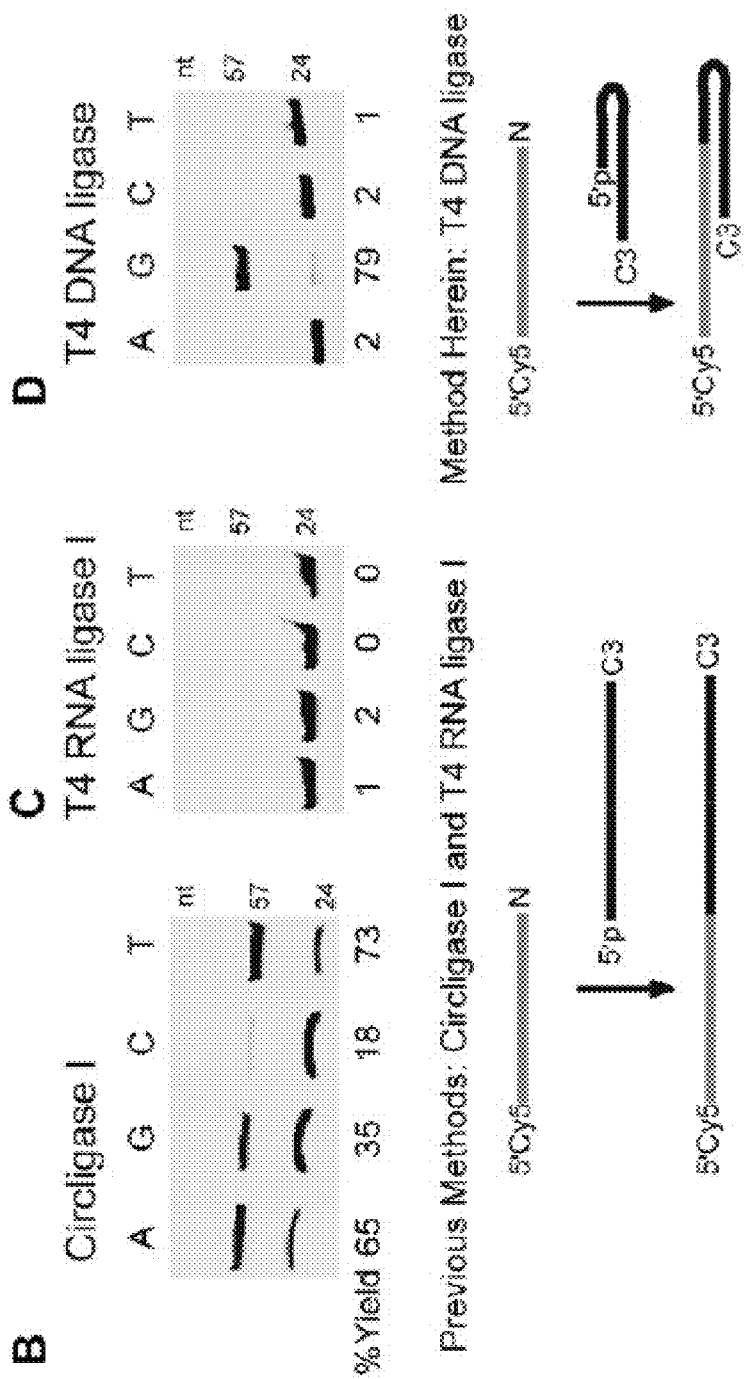
Figure 6:
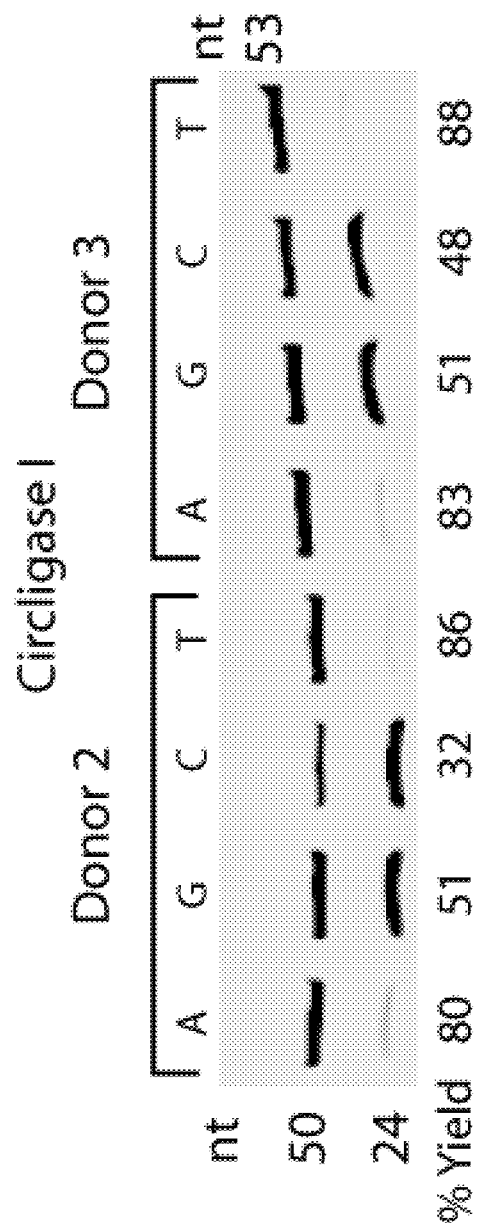
FIG. 6 is an image depicting the results of a nucleotide preference test of donor oligonucleotides 2 and 3 using Circligase I. Donor sequences are provided in FIG. 23. Donor 2 has minimal secondary structure, and Donor 3 has 3 randomized nucleotides at its 5'-end. The reaction contained 100 pmol of 5'p donor, 1 pmol of Cy5-labelled acceptor, 50 mM MOPS (pH 7.5), 10 mM KCl, 5 mM $MgCl_2$, 1 mM DTT, 0.05 mM ATP, 2.5 mM $MnCl_2$ and 200 U Circligase I. Reaction was performed at 65° C. for 12 h, and then 85° C. for 15 min to deactivate the enzyme.

First, the efficiency of Circligase I was tested (FIG. 1B). Ligation of ssDNA with each of the four DNA bases at the 3' end of the acceptor was assessed after 12 h of incubation under the vendor's recommended condition, as discussed elsewhere herein. The yield varied widely, from 18-73%, with a strong acceptor 3' end bias of dT>dA>>dG>>dC (FIG. 1B). Without being bound to any particular theory, it is believed that this trend matched that of the DNA circularization reaction using Circligase I. Similar or slightly improved yields and nucleotide bias were observed when another donor oligonucleotide with minimal secondary structure was used (ranging from 32-86%), or when the first 3 nucleotides of the donor sequence were randomized (ranging from 48-88%) (FIG. 6). These observations suggest that the pooled donor approach used elsewhere (Jayaprakash et al., 2011, Nucleic Acids Res. 39(21):e141) or that using a donor with minimal secondary structure cannot appreciably alleviate the inherent nucleotide bias. In fact, the acceptor Mfold predicted structure (FIG. 1A) did not reveal strong secondary structure at its 3' end, and ligation reaction for Circligase I was performed at 65° C., which likely denatures secondary structure. These findings suggest that such nucleotide bias at the 3'-end of the acceptor is a common feature for Circligase and not due to secondary structure. It was previously reported that Circligase I is a RNA ligase that shows homology to T4 RNA ligase I (Blondal et al., 2005, Nucleic Acids Res. 33:135-142), and it is well known that T4 RNA ligase I has strong preference to ligate to certain end nucleotide over others (Ohtsuka et al, 1977, Eur. J. Biochem. 81: 285-291; Harada et al., 1993, Proc. Natl. Acad. Sci. USA 90:1576-1579; McLaughlin et al., 1982, Eur. J. Biochem. 125:639-643; Rieder et al., 2009, Methods Mol. Biol. 540:15-24), consistent with these observations.

To test the properties of Circligase further, the experiments presented in FIG. 1B were repeated in the presence of 20% PEG 8000 and at 68° C. (Li et al., 2006, Anal. Biochem. 349:242-246). It was found that nucleotide bias was still obvious and the bias spanned 25-64% after 12 h (FIG. 7). These results all suggested that the nucleotide bias in Circligase ssDNA ligation cannot be remediated by rational experimental design. This may not pose a problem for certain applications, such as if quantitative analysis is not required, as in 5' rapid amplification of cDNA ends (D. Bertioli, R. Rapley. (2000) "Rapid Amplification of cDNA Ends" The Nucleic Acid Protocols Handbook, pp 613-617, Humana Press.), where only the 5' most nucleotide of the RNA is of major concern. Notably, without wishing to be bound by any particular theory, if Circligase I is used for ssDNA ligation with acceptors of unknown 3' end, severe sequence bias will result in which the sequence of the RNAs of interest will not be properly represented in the final reaction products. Since Circligase II is the same protein as Circligase I, differing only in adenylation status, it is likely that severe sequence bias will also result if Circligase II is used for ssDNA ligation with acceptors of unknown 3' end.

Next, T4 RNA ligase-mediated ligation of ssDNA was examined. Here the yield was very poor: the ligated product was only ~1% under the examined conditions (FIG. 1C). As such the nucleotide preference cannot be assessed. Consistent with observations presented herein, T4 RNA ligase I was previously shown to be less efficient than Circligase I for ssDNA ligation (Blondal et al., 2005, Nucleic Acids Res. 33:135-142) and required PCR amplification to obtain observable products (Zhang et al., 1996, Nucleic Acids Res. 24:990-991). It is noted that both Circligase- and T4 RNA ligase-mediated ligation of ssDNA occur in a template-independent fashion, as depicted in at the bottom of FIG. 1B-FIG. 1D.

Initial Tests of ssDNA Ligation Using T4 DNA Ligase

Next, ssDNA ligation using T4 DNA ligase was attempted. To obtain the optimal condition for ligation, factors that could contribute to ligation efficiency were tested. It was found that 20% PEG 8000, 0.5M betaine, and 100:1 donor:acceptor ratio resulted in high (>80%) ligation yield of the acceptor at 16° C. and 3 h (FIGS. 9-15). Initially, the nucleotide preference test described above for Circligase I showed that T4 DNA ligation was efficient only when the acceptor 3'-end was a "G" residue (FIG. 1D). It is well-known that T4 DNA ligase mostly acts on a dsDNA junction (Nilsson et al., 1982, Nucleic Acids Res. 10: 1425-1437; Alexander et al., 2003, Nucleic Acids Res. 31:3208-3216; Lehman, 1974, Science 186:790-797), although template-independent T4 DNA ligation of ssDNA has also been reported, albeit at a very low efficiency (Kuhn and Frank-Kamenetskii, 2005, FEBS J 272:5991-6000). Sequence-specific ligation (FIG. 1D, top) suggested that intra- and intermolecular DNA secondary structure could be influencing the ligation. This suggested a model in which a dsDNA junction was formed between the donor and acceptor for ligation to occur (FIG. 1D, bottom).

To better understand the ligation result, Mfold was used to predict the secondary structure of the ligated DNA product. This revealed intermolecular base pairing of the acceptor and donor, similar to a primer-template model. While not wishing to be bound by any particular theory, a possible mode of reaction was shown in FIG. 2. From this model, it is reasoned that the low ligation efficiency with the other bases at the 3'-end of the acceptor (FIG. 1D, top) might be due to the presence of a mismatch between the acceptor and donor at the ligation junction, which is herein referred to as 24':18. Although the ligation using T4 DNA ligase requires base pairing at the junction, this reaction is herein regarded as ssDNA ligation because both acceptor and donor are single strands.

Hairpin Donor Design and Mutational Studies

Figure 2:
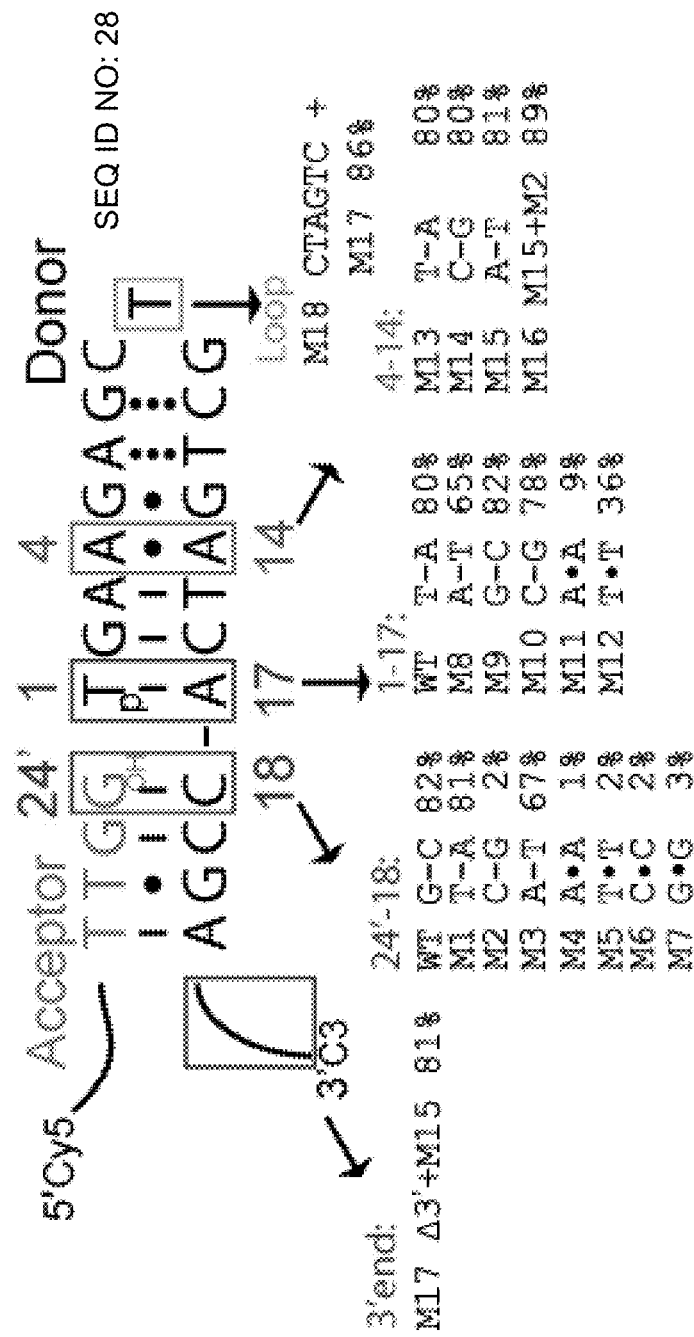
FIG. 2 depicts a ligation model for ssDNA ligation using T4 DNA ligase and positions and identities of DNA mutations. These reactions were in 20% PEG 8000, 0.5 M betaine, 100:1 donor:acceptor ratio, and 15 U T4 DNA ligase for 12 h at 16° C. SEQ ID NO: 28 represents the depicted portion of the donor molecule. The mini-hairpin (nucleotides 22-33) of the donor sequence is shown in FIG. 1A. Although base pairs 6:12 and 7:11 shown on FIG. 2 (dotted) were not predicted by Mfold using the WT donor (FIG. 1A), they were predicted to form when base pair 4:14 was changed to WC base pair (M13-M15). In addition, it was reasoned that under conditions where 20% PEG was added, these base pairs may form. For gels showing ligation results of M1-M18, see FIGS. 16-21.
Figure 16:
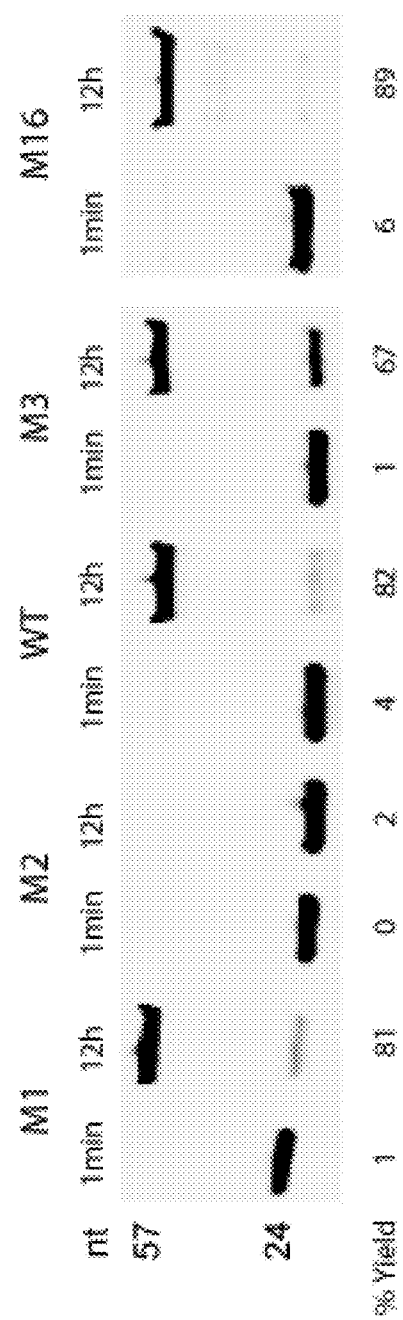
FIG. 16 is an image depicting the results of ssDNA ligation of M1-M3, M16 and WT using T4 DNA ligase. The ligation reaction contained 100 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5M betaine. The reaction was performed at 16° C. for 12 h, and then 65° C. for 15 min to deactivate the enzyme.
Figure 17:
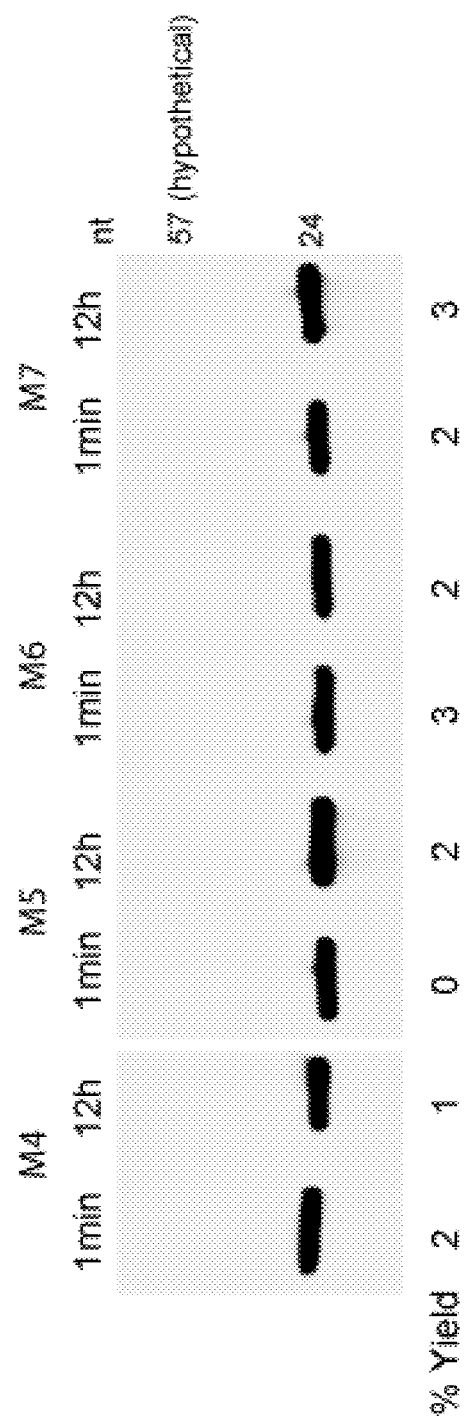
FIG. 17 is an image depicting the results of ssDNA ligation of M4-M7 using T4 DNA ligase. The ligation reaction contained 100 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5M betaine. The reaction was performed at 16° C. for 12 h, and then 65° C. for 15 min to deactivate the enzyme.

To test the hypothesis that acceptor-donor mismatch was impairing ligation of non-G terminated acceptors, a series of mutational studies were performed. First, it was attempted to rescue ligation efficiency of acceptor 3'-ends T, C, and A by restoring the 24':18 base pairing (FIG. 2; see mutants M1, M2, and M3, respectively). M1 and M3 showed marked improvements in yield, from just 1% and 2% to 81% and 67%, respectively (FIGS. 2 and 16). M2, however, still had a low yield of 2%. While not wishing to be bound by any particular theory, secondary structure prediction revealed that this was likely due to an alternative structure of the donor, which hindered base pairing of the acceptor. In an effort to limit this alternative structure, the native hairpin structure of the donor was strengthened by introducing Watson-Crick (WC) base pairing at position 4:14, far from the site of ligation (FIG. 2) (see M13-M15). It is shown that these changes were compatible with efficient ligation in the presence of a 3'-end G acceptor, where they actually increased the kinetics of ligation somewhat (compare 1 min lanes in FIGS. 16 and 20). Importantly, WC base pairing at 4:14 rescued M2, (see M16=M15+M2) with a ligation efficiency of 89% (FIGS. 2 and 16). Thus, native donor hairpin structure contributes to achieving efficient ligation. After confirming that all WC base pairs at 24':18 are efficiently incorporated, the 4 homonucleobase mismatches at the 24':18 base pair were tested (see M4-M7). None of these mutants gave appreciable ligated product, even after 12 h (just 1-3% yield) indicating that the T4 DNA ligation of ssDNA has fidelity of base pair recognition with the 3'-end of the acceptor (FIGS. 2 and 17).

Figure 18:
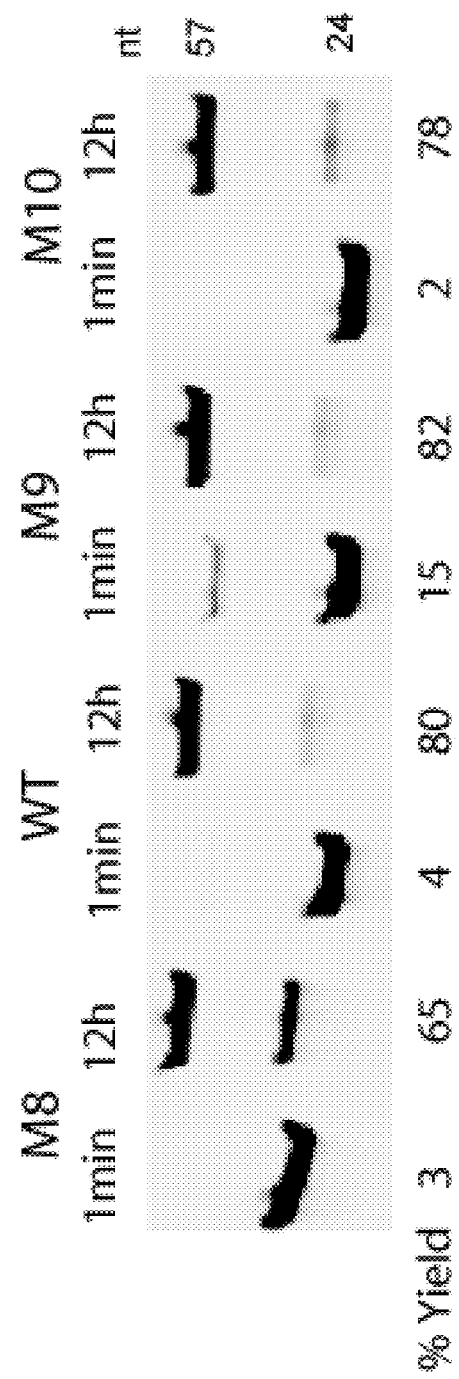
FIG. 18 is an image depicting the results of ssDNA ligation of M8-M10 and WT using T4 DNA ligase. The ligation reaction contained 100 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5M betaine. The reaction was performed at 16° C. for 12 h and then 65° C. for 15 min to deactivate the enzyme. The 1 min samples were loaded and ran slightly before the 12 h samples.
Figure 19:
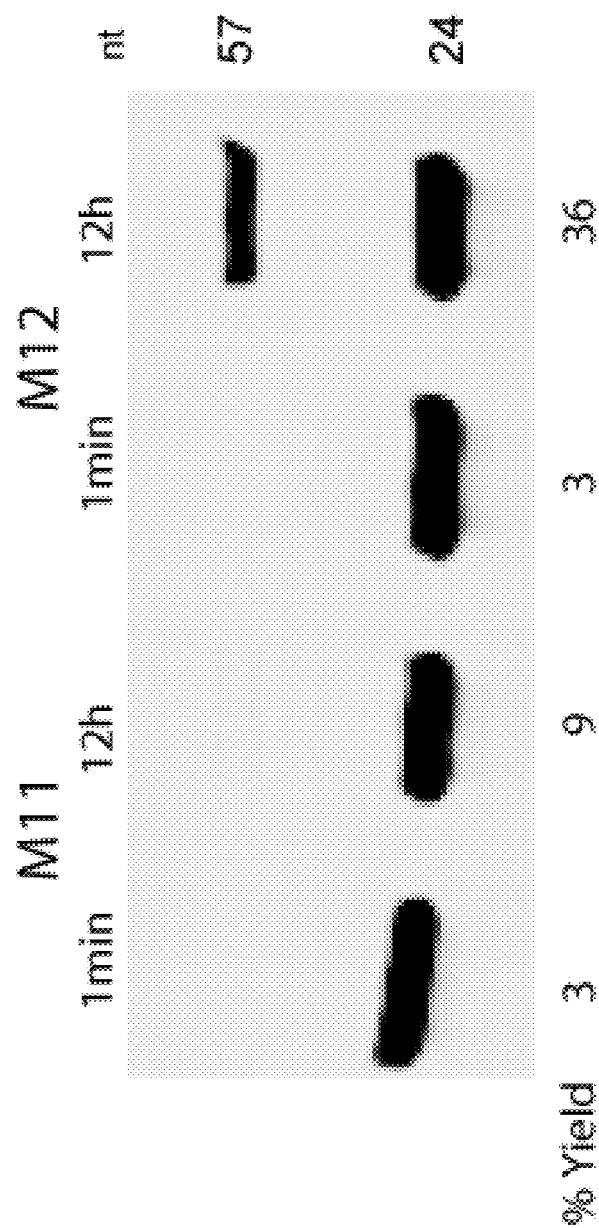
FIG. 19 is an image depicting the results of ssDNA ligation of M11-M12 using T4 DNA ligase. The ligation reaction contained 100 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5 M betaine. The reaction was performed at 16° C. for 12 h, and then 65° C. for 15 min to deactivate the enzyme.

Using the same rationale, the importance of the 5'-end of the donor was tested for ligation efficiency via the terminal base pair 1:17 (FIG. 2). Efficient ligation was observed with all three other WC base pairs at 1:17, M8-M10 (FIGS. 2 and 18). Changing the 1:17 base pair to an AA or TT mismatch, however, reduced the ligation yield to 9 and 36%, respectively (FIGS. 2 and 19). While not wishing to be bound by any particular theory, the intermediate yield observed for the TT mismatch at the 1:17 base pair is likely due to formation of a two hydrogen bond wobble base pair owing to intramolecular folding of the donor. Such an intramolecular wobble TT mismatch formation has been observed previously by NMR spectroscopy (He et al., 2011, FEBS Lett. 585:3953-3958). Overall, the T4 DNA ligation of ssDNA has fidelity of base pairing for both base pairs flanking the ligation junction.

Figure 20:
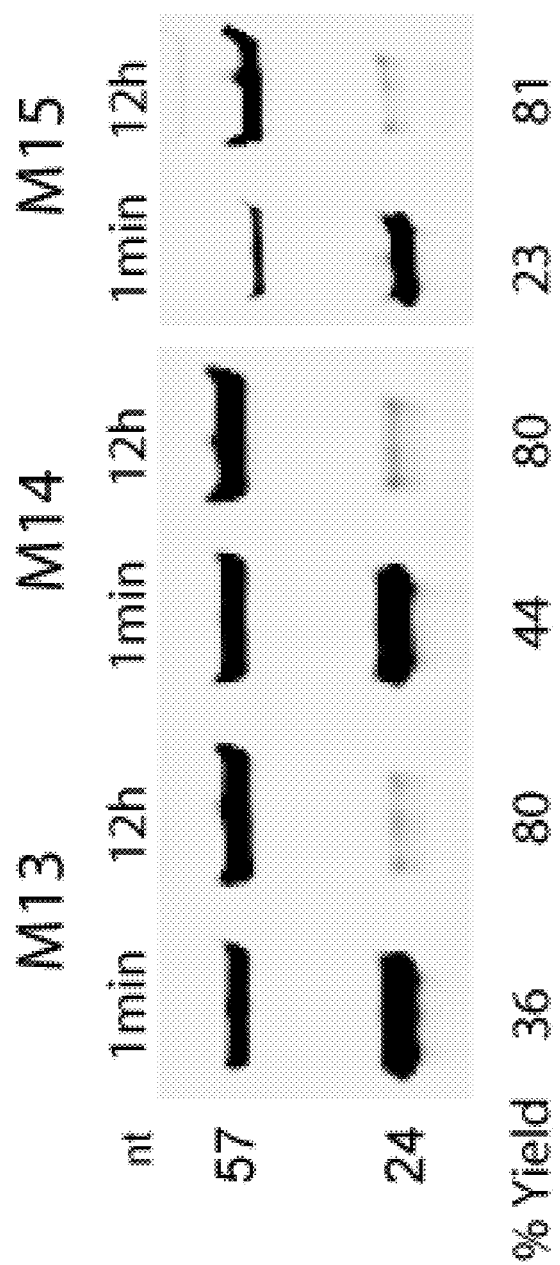
FIG. 20 is an image depicting the results of ssDNA ligation of M13-15 using T4 DNA ligase. The ligation reaction contained 100 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5 M betaine. The reaction was performed at 16° C. for 12 h, and then 65° C. for 15 min to deactivate the enzyme.
Figure 21:
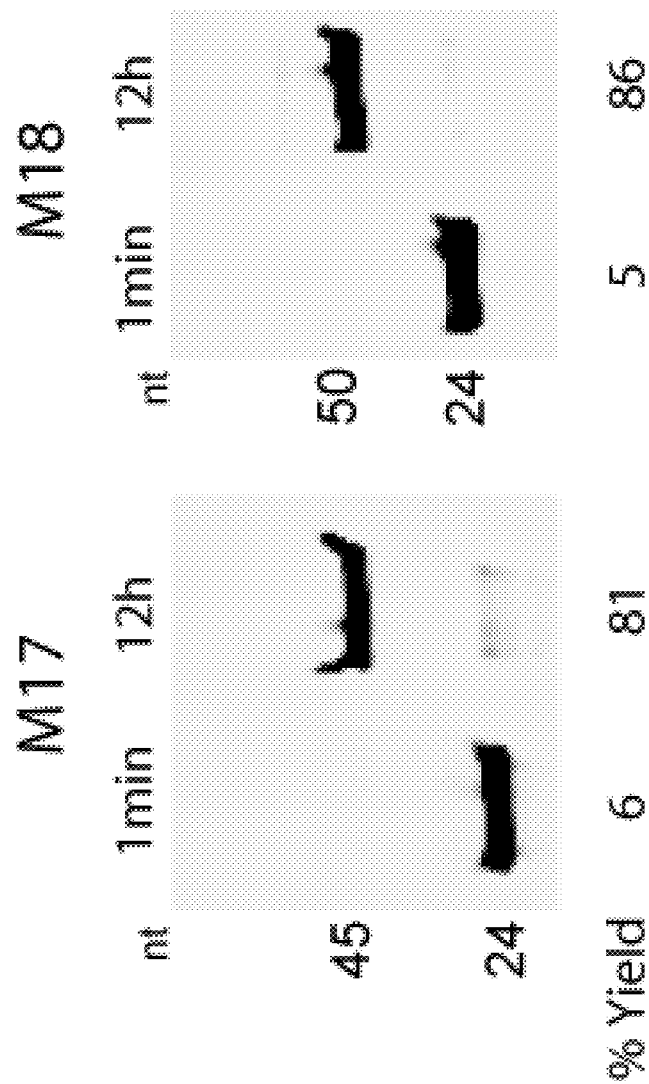
FIG. 21 is an image depicting the results of ssDNA ligation of M17 and M18 using T4 DNA ligase. The ligation reaction contained 100 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5 M betaine. The reaction was performed at 16° C. for 12 h and then 65° C. for 15 min to deactivate the enzyme.

Lastly, the importance of the 3'-end and the loop of the donor was tested. The ligation yield of a 3'-end deletion mutant, M17, was 81% after 12 h, although the kinetics was somewhat slower (FIGS. 20 and 21). While not wishing to be bound by any particular theory, one possible reason for a slower rate is that the 3'-overhang present in the full length donor, but absent in the mutant, forms a mini-hairpin (FIG. 1) that may reduce alternative structure. A loop mutant, M18, that changed the apical T to the larger non-WC base paired hexaloop of CTAGTC was made and had a slightly increased yield of 86%, which, while not wishing to be bound by any particular theory, could be due to formation of the 8:10 CG base pair, previously precluded by the smaller loop (FIGS. 2 and 21) (Shu and Bevilacqua, 1999, Biochemistry 38:15369-15379). There are two potential advantages to having a larger hairpin loop in the donor: i) it can help avoid donor-donor dimerization, which could hinder ligation, and; ii) it can provide part of a primer binding site and thus increase the melting temperature of the primer used in PCR for downstream applications.

Optimized ssDNA Ligation Using T4 DNA Ligase

For application to a LMPCR type experiment, the 3'end of the acceptor is likely to be truncated and thus have different sequences from the full-length cDNA generated from reverse transcription. Therefore, a general donor oligonucleotide (40mer) was designed by introducing a random hexamer region that can hybridize with different incoming acceptors. It was tested whether this donor could ligate efficiently and in an unbiased manner to various acceptors (FIG. 3A). This donor also contains the mini-hairpin as a 3'-overhang since this promoted more efficient kinetics. The rationale for constructing a random hexamer region to widely target acceptor sequences in single-stranded DNA ligation is similar to the idea for random hexamer priming in reverse transcription, wherein use of random hexamers enables targeting of diverse RNA sequences. To evaluate this donor, the nucleotide preference ligation test was performed on four 24mer acceptors each with a different base at its 3' end. The ligation efficiencies for the individual acceptors were very similar to one another, with average yields of 93±1%, 90±1%, 96±1%, 95±1% for A, G, C and T, respectively (FIG. 3B). This outcome contrasts sharply with the data in FIG. 1D, where only one of the four acceptors ligated efficiently. Moreover, this result provides much less bias as compared to Circligase I (FIG. 1A, FIG. 6 and FIG. 7).

Figure 3:
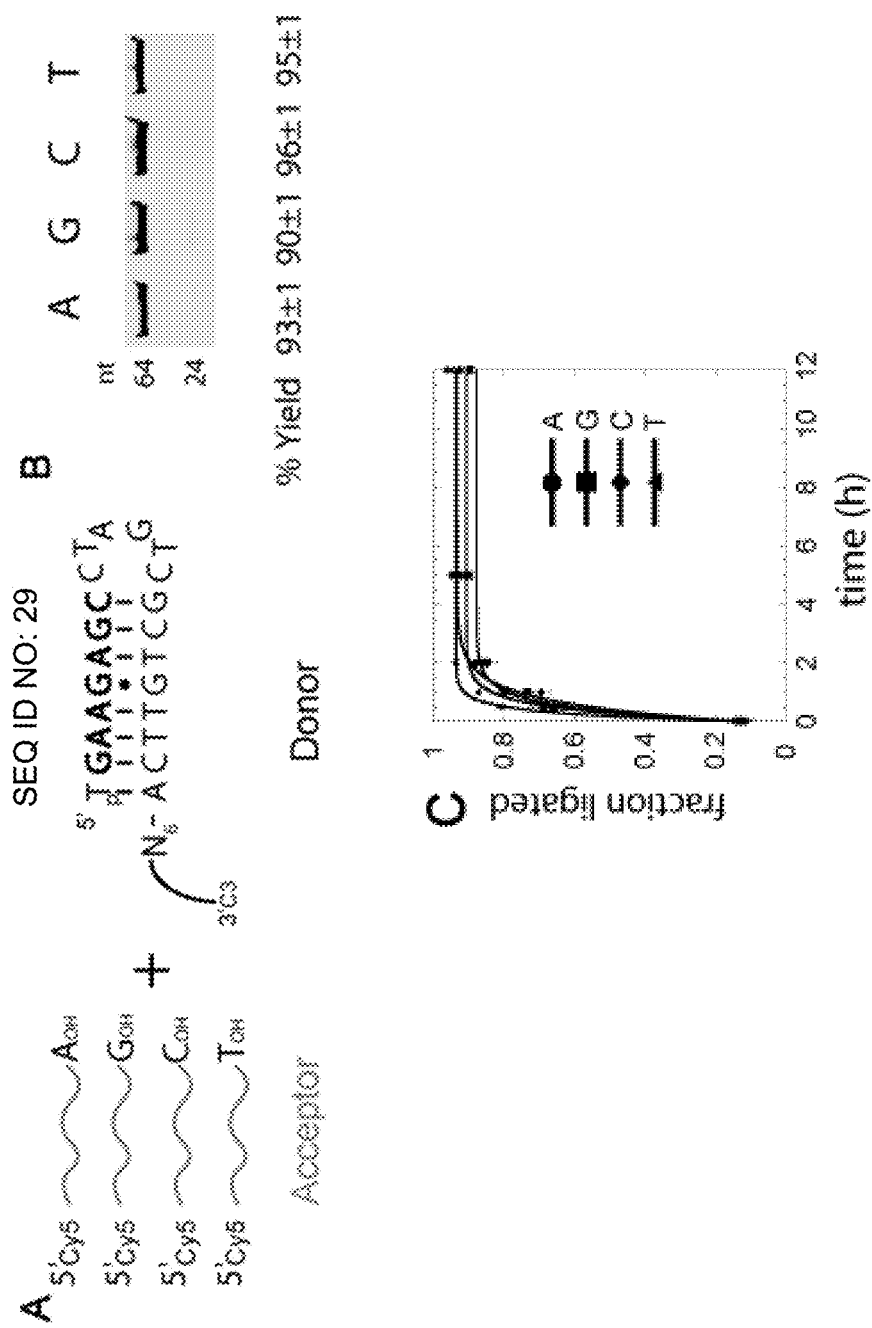
FIG. 3, comprising
Figure 4:
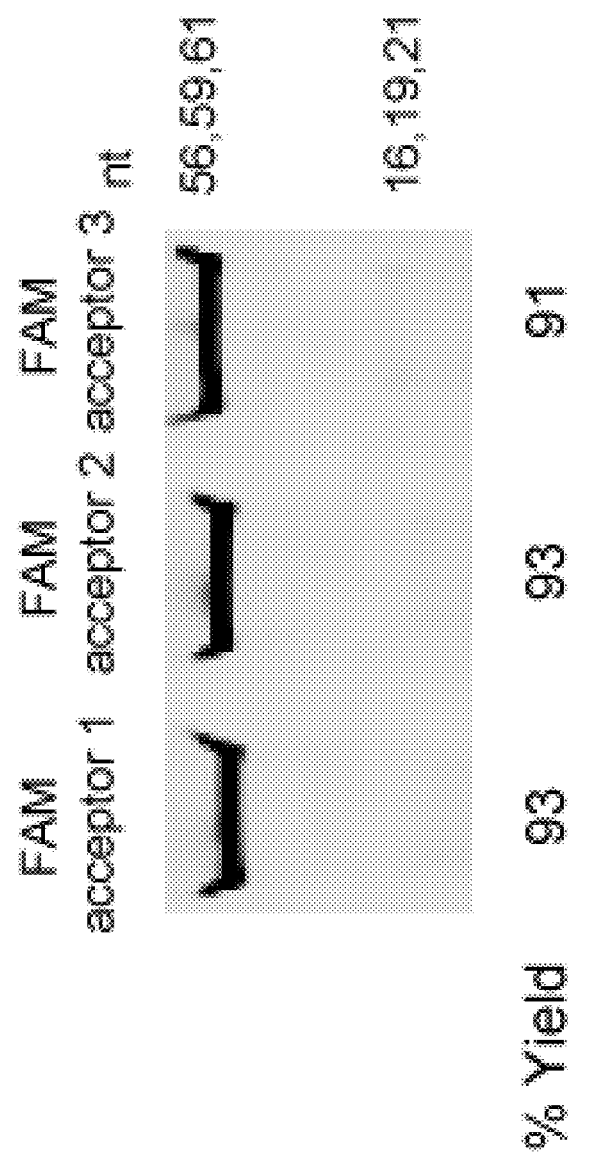
FIG. 4 is an image depicting the results of experiments examining ssDNA ligation of optimized donor (40mer) and 3 additional FAM labeled acceptors (16, 19, 21mer) using T4 DNA ligase. Reactions were in 20% PEG 8000, 0.5 M betaine, 100:1 donor:acceptor ratio, and 15 U T4 DNA ligase for 12 h at 16° C. Samples were fractionated on a 10% urea-polyacrylamide gel and subjected to PhosphorImager scanning.
Figure 22:
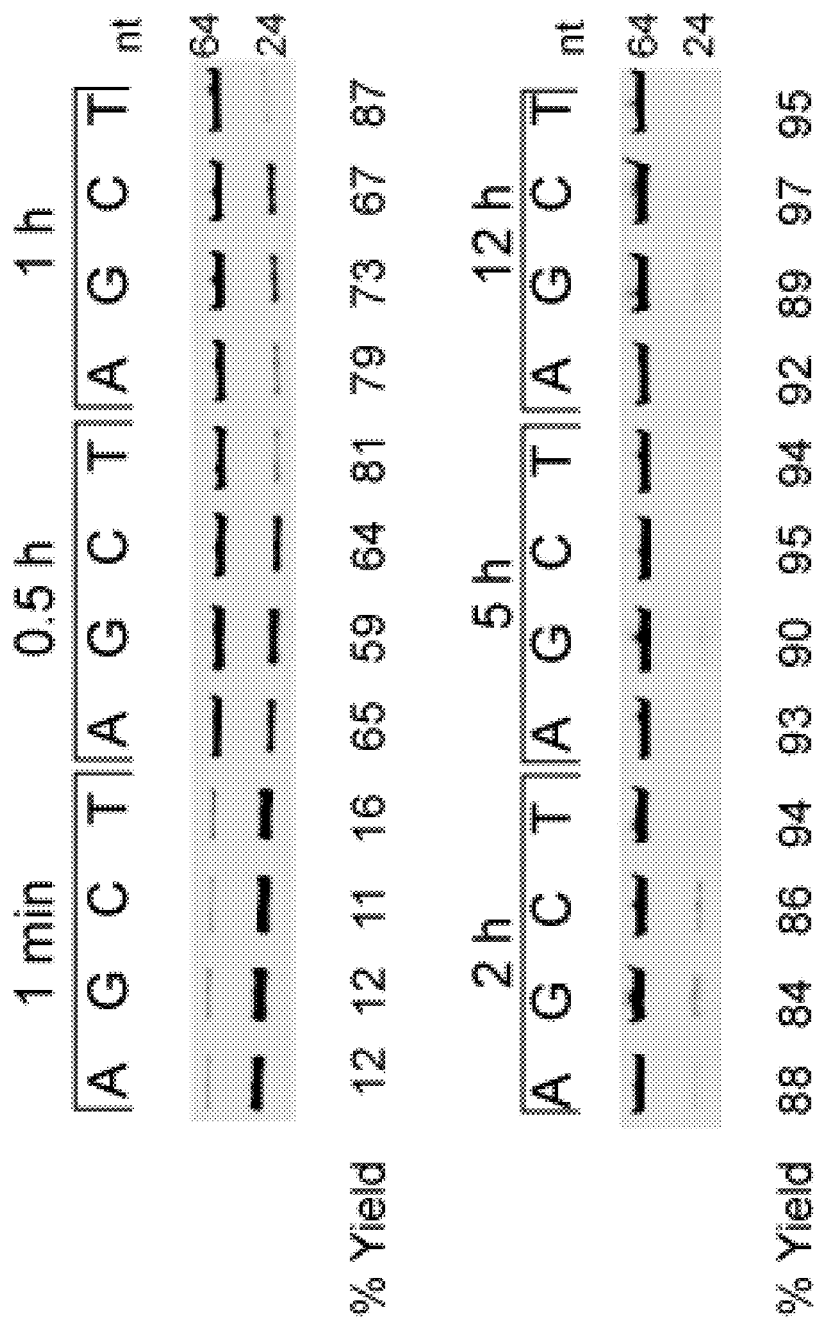
FIG. 22 is an image depicting the results of experiments examining ssDNA ligation kinetics and nucleotide preference of optimized construct using T4 DNA ligase. The ligation reaction contained 400 pmol of 5'p donor, 1 pmol of Cy5-labelled acceptor, 50 mM Tris-HCl (pH 7.5), 10 mM $MgCl_2$, 10 mM DTT, 1 mM ATP, 20% PEG 8000 and 0.5 M betaine. The reaction was performed at 16° C. 400 pmol of 5'p donor was used since only ¼ of the donor molecules had the complementary nucleotide that matched the 3' end nucleotide of the acceptor.
Figure 24:
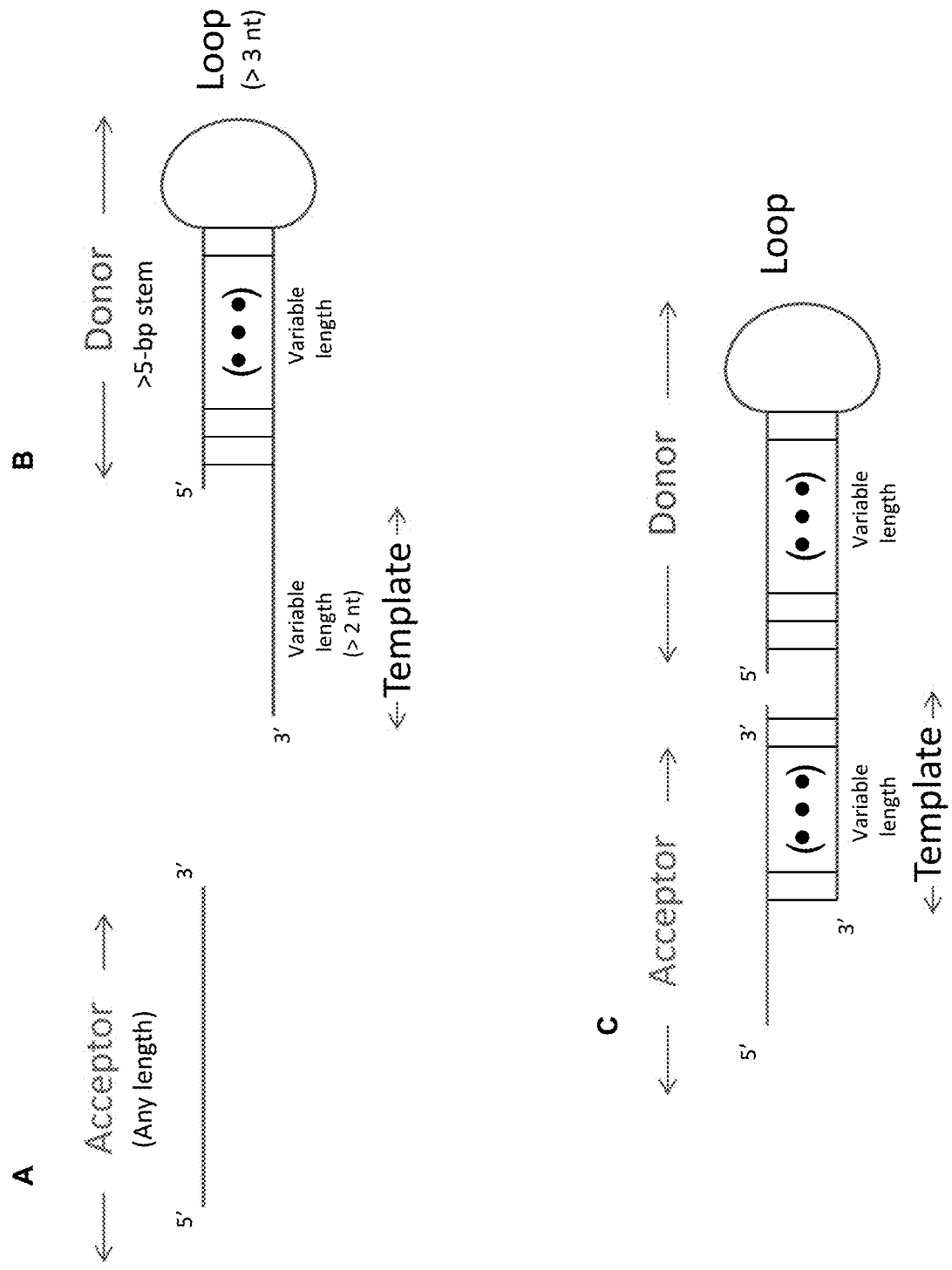
FIG. 24, comprising

Next the kinetics of the T4 DNA ligase-mediated ssDNA ligation reaction was tested using the optimized donor with a hexaloop and a random hexamer template region. A first-order rate constant of >2 or >50% reaction in less than 30 min (FIGS. 3C and 22), was found. To evaluate whether this optimized donor can ligate to other acceptors, 3 additional acceptors with varying sequence were tested, and it was found that the yield were just as efficient as mentioned above (FIG. 4). Given the quantitative and low-bias nature of the template-mediated approach, as illustrated in FIG. 3, FIG. 4, and FIG. 22, this approach differs significantly from the Circligase method mentioned above, in not requiring correction for nucleotide bias with a statistical correction factor.

Potential Applications of Optimized Hairpin Donor

Figure 5:
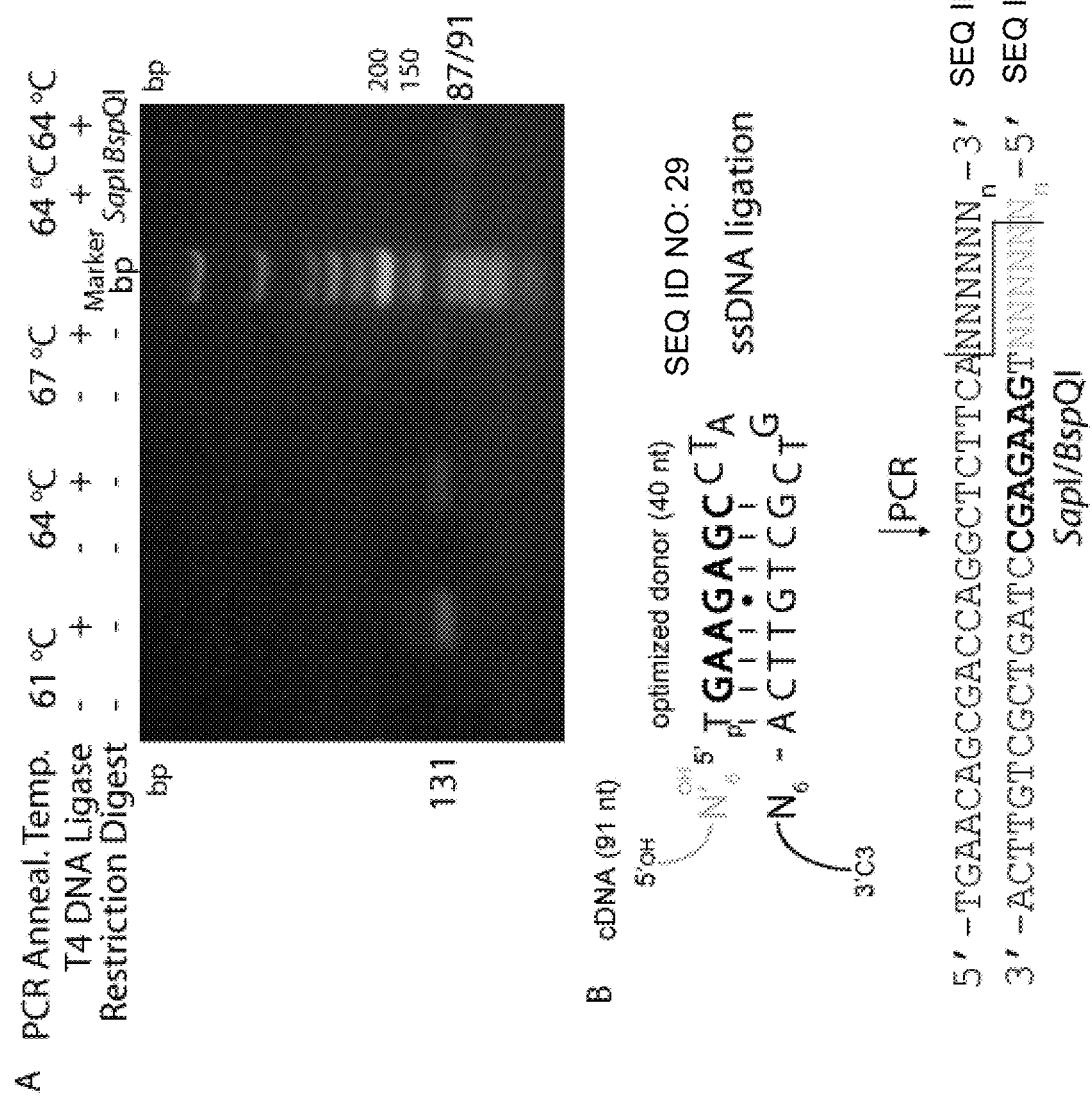
FIG. 5, comprising

To test the general applicability of the ssDNA ligation method described herein, it was sought to mimic ligation of the longer cDNAs that would be generated during reverse transcription. A 91 nucleotide DNA acceptor was designed that contains hydroxyl groups at both termini. This acceptor was subjected to ssDNA ligation with the 40mer donor from FIG. 3, and product formation was followed by PCR. A 131-bp PCR product formed in a T4 DNA ligase-dependent fashion (FIG. 5). This result indicated that the hairpin donor can be used for LMPCR. It should be noted that although this approach requires a hairpin stem and a random templating region, the hairpin stem can be varied to other WC base pair combination (see FIG. 2) to avoid any sequence complementary to the gene of interest and mis-priming during PCR reaction. Also, it should be noted that any strong secondary structure at the 3' end of the DNA acceptor may interfere with the hybridization and thus the ligation efficiency. A locked nucleic acid (LNA) base at the randomized templating region may be designed and introduced to allow more efficient hybridization (Fratczak et al., 2009, Biochemistry 48(3):514-6). In addition, low amounts of DMSO (5-10%) often help to improve reactivity of protein enzymes that act on nucleic acids, such as tRNA ligase and polynucleotide kinase (PNK), at the ends of structured RNAs (Bruce and Uhlenbeck, 1978, Nucleic Acids Res. 5:3665-3678; Strauss et al., 1968, Biopolymers 6:793-807).

It is noted that for next generation sequencing, the platform-specific adaptor (donor) has to be ligated in an early step of cDNA library construction, such as in the SHAPE-Seq application (Lucks et al., 2011, Proc. Natl. Acad. Sci. USA 108:11063-11068). Various sequencing platforms for next-generation sequencing are available, and the choice of a specific platform will likely be influenced by sequencing cost, instrument availability, and user application. Therefore, during development of the hairpin donor described herein, a 7 nucleotide Type IIS restriction site (SapI/BspQI) was incorporated, which provides the user an option to remove the donor after PCR amplification, if needed (FIGS. 3 and 5). On the one hand, the advantage of retaining the donor sequence, including the restriction enzyme site, is that it can provide an internal check of the 3' end of the acceptor DNA, as the sequencing result should have donor sequence immediately followed by acceptor sequence. On the other hand, if the donor is removed by SapI/BspQI restriction digest, the digested dsDNA pool can also be subjected to routine processing as required for the production of next-generation sequencing libraries, including the steps of end-repair, dA tailing and platform sequence-specific double-stranded adaptor ligation. This general approach allows the decision for next generation sequencing platform to be made at the last step, and allows cross-platform validation (Linsen, et al., 2009, Nat. Meth. 6:474-476; Potapova et al., 2011, BMC Biotechnology 11:6) on the same or different cDNA library sample, as the digested dsDNA pool can be re-used for different platforms. This is in contrast to some cDNA library preparation methods, such as SHAPE-Seq, in which a platform-specific adaptor sequences has to be ligated in an early step and such adaptor sequences usually only work in a single platform. Lastly, the high throughput data obtained will have greatly reduced sequence bias.

In summary, described herein is a fast, efficient, and low-bias method for ligating two ssDNAs. A hairpin donor DNA hybridizes with different acceptor 3'-end to yield the desired ligation product (FIG. 3B). The reaction uses the common enzyme T4 DNA ligase and is completed in 2 h. The method provides an alternative approach for ssDNA ligations that can be applied to LMPCR, and allows platform-free cDNA library construction, including for cross-platform validation. It can also be used as a tool to develop new biochemical and molecular biology methods. Lastly, this ssDNA ligation method can also be used in a sequence-specific mode to allow only certain acceptor 3'-ends to give a ligation product (e.g. FIG. 1D), which provides an approach for selecting specific sequences from a 3'-end pool.

Example 2: Determination of In Vivo RNA Structure in Low-Abundance Transcripts

RNA is of central importance in gene regulation, catalysis and the origin of life (Gesteland, R. F., et al., Cold Spring Harbor Laboratory Press, 2006.). Numerous classes of RNA perform key biological functions via folding into diverse structures. Knowledge of RNA structure in vivo therefore provides important insights regarding the evolution and function of biological systems. However, the structures of all but the few most abundant RNAs have been unknown in vivo.

For decades, chemical and enzymatic probing have been among the most common and powerful assays available to obtain structural information on RNA at nucleotide resolution (Ehresmann, C. et al., Nucleic Acids Res. 15:9109-9128, 1987; Stern, S., et al., Science 244:783-790, 1989; Weeks, K. M., Curr. Opin. Struct. Biol. 20:295-304, 2010 and Ding, F., et al., Nat. Meth. 9:603-608, 2012). This information can dramatically improve secondary structure prediction (Mathews, D. H. et al., Proc. Natl Acad. Sci. USA 101:7287-7292, 2004; Low, J. T. et al., Methods 52:150-158, 2010 and Cordero, P., et al., Biochemistry 51:7037-7039, 2012). Structures generated provide insights regarding the control of RNA transcription, processing, stability, translation and ligand-binding.

Among RNA structural probing reagents, dimethyl sulfate (DMS) is highly versatile and useful for in vivo probing (Zemora, G. et al., RNA Biol. 7:634-641, 2010), owing to its ability to penetrate cells and modify RNA in numerous organisms (Moazed, D., et al., Nature 334:362-364, 1988; Senecoff, J. F. et al., Plant Mol. Biol. 18:219-234, 1992; Zaug, A. J. et al., RNA 1:363-374, 1995; Higgs, D. C., et al., Mol. Cell Biol. 19:8479-8491, 1999; Wells, S. E., et al., Methods Enzymol. 318:479-493, 2000; Iseni, F., et al., RNA 6:270-281, 2000 and Antal, M., et al., Nucleic Acids Res. 30:912-920, 2002). Recently, in vivo SHAPE reagents were developed and have been used to probe the highly abundant 5S rRNA in bacteria, yeast, fly and mammalian cells (Spitale, R. C. et al., Nat. Chem. Biol. 9:18-20, 2013). DMS methylates the N1 of adenine and the N3 of cytosine on the Watson-Crick base pairing face of unprotected regions such as loops, bulges and mismatches (Zaug, A. J. et al., RNA 1:363-374, 1995 and Wells, S. E., et al., Methods Enzymol. 318:479-493, 2000), whereas SHAPE reagents acylate the 2'-hydroxyl group on the ribose sugar of unstructured regions of all four nucleotides (Spitale, R. C. et al., Nat. Chem. Biol. 9:18-20, 2013 and Wilkinson, K. A., et al., Nat. Protoc. 1:1610-1616, 2006). Methylation or acylation chemistry is detected by reverse transcription (RT) stops one nucleotide before the modified nucleotide (Zaug, A. J. et al., RNA 1:363-374, 1995; Wells, S. E., et al., Methods Enzymol. 318:479-493, 2000; Spitale, R. C. et al., Nat. Chem. Biol. 9:18-20, 2013; Wilkinson, K. A., et al., Nat. Protoc. 1:1610-1616, 2006 and Inoue, T. et al., Proc. Natl Acad. Sci. USA 82:648-652, 1985).

In cellular systems, structures of high-abundance RNAs such as rRNA can be assessed in vivo by a DMS/SHAPE-RT approach (Senecoff, J. F. et al., Plant Mol. Biol. 18:219-234, 1992; Zaug, A. J. et al., RNA 1:363-374, 1995; Wells, S. E., et al., Methods Enzymol. 318:479-493, 2000 and Spitale, R. C. et al., Nat. Chem. Biol. 9:18-20, 2013). However, the vast majority of RNAs in a typical cell are of low abundance in vivo and cannot be explored by an RT-based approach. As such, very little is known about the in vivo structures of myriad RNAs, including most mRNAs and non-coding (nc) RNAs, despite their essential roles in protein synthesis and other cellular processes. Moreover, the effects of RNA-binding proteins on in vivo RNA structures are also largely unexplored.

As described by Kwok et al., (Kwok et al, 2013, Nature Communications, 4: article number: 297), the contents of which are incorporated by reference herein in their entirety, a sensitive method was developed that is able to detect rare RT products in order to probe the structures of low-abundance RNAs in living cells. This method increases the sensitivity of detection 100,000-fold over the conventional RT-based method. It is demonstrated that both DMS and SHAPE chemistries permit in vivo RNA structural probing in *Arabidopsis thaliana*, an important model plant species and eukaryote. Notably, the in vivo SHAPE reagent, 2-methylnicotinic acid imidazolide (NAI) (Spitale, R. C. et al., Nat. Chem. Biol. 9:18-20, 2013) was employed, and the first examples of in vivo SHAPE probing in plants were presented. The RT-based method (FIG. 25, first three steps) was used to successfully query the structures of rRNA (25S rRNA and 5.8S rRNA) and chloroplast mRNA (PSBA) in *A. thaliana*. Then, a selective amplification strategy was developed to establish a highly sensitive and robust method, 'DMS/SHAPE-LMPCR', which uses ssDNA ligation, and achieves a 5-log enhancement in sensitivity. Using this LMPCR-based approach (FIG. 25, all five steps), DMS/SHAPE modification signals were uncovered from low-abundance RNAs, and their RNA structures are revealed for the first time in vivo.

As demonstrated herein, DMS/SHAPE-LMPCR, using ssDNA ligation, achieves attomole sensitivity, a 100,000-fold improvement over conventional methods. The structure of low-abundance U12 small nuclear RNA (snRNA) is probed in *Arabidopsis thaliana* and in vivo evidence is provided supporting the derived phylogenetic structure. Interestingly, in contrast to mammalian U12 snRNAs, the loop of the SLIIb in U12 snRNA is variable among plant species, and DMS/SHAPE-LMPCR determines it to be unstructured. The effects of proteins on 25S rRNA, 5.8S rRNA and U12 snRNA structure is revealed, illustrating the critical importance of mapping RNA structure in vivo. The universally applicable method opens the door to identifying and exploring the specific structure-function relationships of the multitude of low-abundance RNAs that prevail in living cells.

Figure 25:
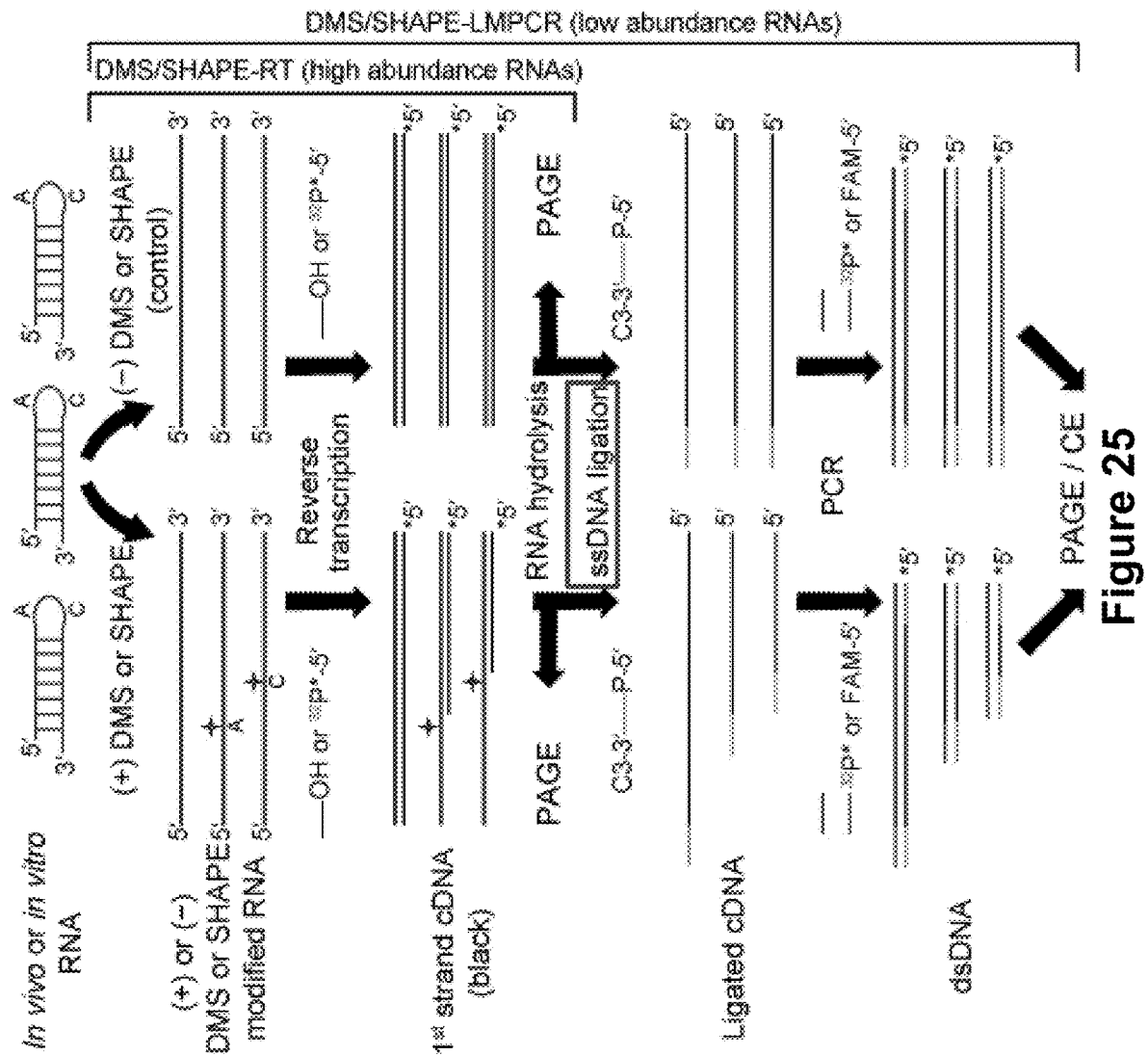
FIG. 25 depicts a flow chart for the targeted determination of RNA structure for high- and low-abundance RNAs. Either DMS/SHAPE-RT (Steps 1-3) or DMS/SHAPE-LMPCR can be used (all steps). In the first step, total RNA is treated with DMS or SHAPE reagent, either in vitro or in vivo. In DMS/SHAPE-RT, a radiolabeled 5'-$^{32}$P gene-specific primer is used for the RT step, whereas in DMS/SHAPE-LMPCR, an unlabelled 5'-OH gene-specific primer is used for the RT step. Next, the RNA is degraded by base hydrolysis. For DMS/SHAPE-LMPCR, the unlabelled cDNA generated from RT is ligated to a DNA adaptor by single-stranded (ss) DNA ligation. Subsequently, a 5'-OH DNA adaptor-specific forward primer and a radioactive 5'-$^{32}$P (for PAGE) or a 5'-FAM (for CE) gene-specific nested reverse primer are used for PCR amplification of the ligated cDNA fragments. For the (−)DMS/SHAPE control reaction, all steps are the same except that DMS/SHAPE treatment is omitted.

The sensitivity limits of the standard in vivo RT-based assay were first determined, using DMS probing reagent as an example. The total input RNA was serially diluted until the observable DMS modification pattern for 5.8S rRNA was lost. It was found that a relatively large amount of 5.8S rRNA (~1 pmol) is necessary for conventional DMS-RT. This is approximately the amount of 5.8S rRNA found in 2 µg of a 'total RNA' extraction, which immediately presents a problem if one wants to assay the many much lower abundance RNAs. Without a new approach an RNA at 100,000-fold lower abundance than 5.8S rRNA would require ~0.2 g of total RNA input for the DMS-RT assay, which is clearly impractical. To improve sensitivity, an amplification-based method was explored and developed, which is referred to as 'DMS/SHAPE-LMPCR' (FIG. 25, all steps). In this approach, a DNA adaptor is ligated to the 3' end of the complementary DNA (cDNA), and the ligated cDNA is PCR amplified using a gene-specific and an adaptor-specific primer. With this approach, it was found that the DMS modification pattern of 5.8S rRNA is observable even at a 10-attomole ($10^{-17}$) level of 5.8S rRNA input, which represents a remarkable 100,000-fold enhancement in sensitivity. Notably, the modification pattern derived from DMS-LMPCR was consistent with the pattern derived from the standard DMS-RT data, with strong Pearson correlation coefficient (PCC) between the normalized DMS reactivities for different regions of 5.8S rRNA ranging from 0.72 to 0.82.

Figure 26:
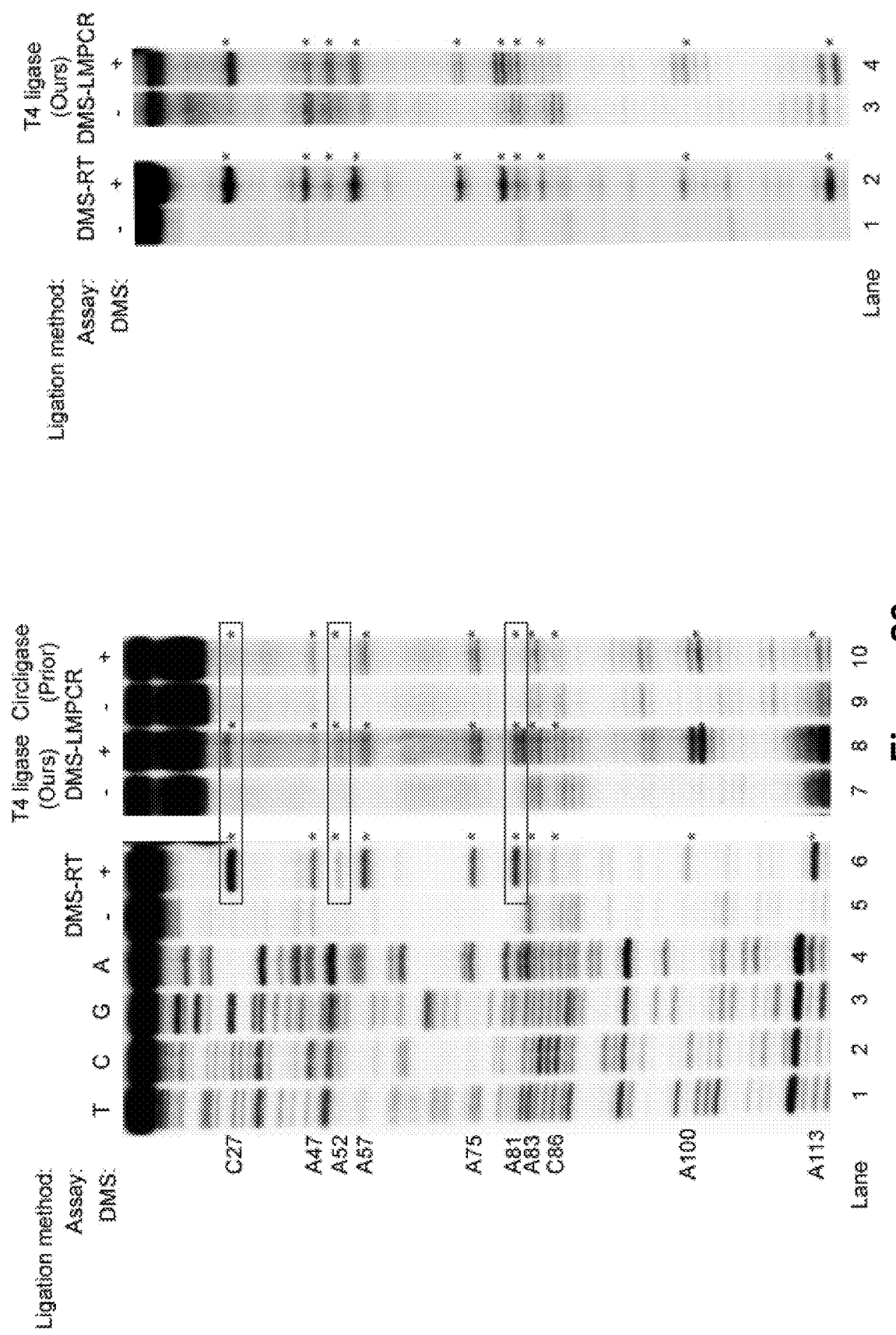
FIG. 26 depicts the results of an experiment comparing DMS/SHAPE-RT with DMS/SHAPE-LMPCR on *Arabidopsis thaliana* 5.8S rRNA using either T4 DNA ligase or Circligase I. Rectangles depict new bands observed only by T4 DNA ligase method (left panel, lane 8) and not by existing Circligase method (left panel, lane 10). Compare lanes 8 and 10 (left panel) to the low sensitivity method of DMS-RT (left panel, lane 6). Asterisks denote bands in lane 6 (left) and where corresponding LMPCR band should be in lanes 8 and 10 (left), (missing for some bands in lane 10). The gel on the right panel is a technical replicate for DMS/SHAPE-RT and DMS/SHAPE-LMPCR (using T4 DNA ligase) on 5.8S rRNA.

Experiments were also conducted to compare the ssDNA ligation method of the invention to the prior Circligase-based ssDNA ligation method. These data demonstrate that the ssDNA ligation method of the invention, using T4 DNA ligase, provides more quantitative results in DMS-LMPCR than Circligase-based ssDNA ligation, using *Arabidopsis thaliana* 5.8S rRNA as an example. For example, FIG. 26, depicts the results of comparison experiments, comparing the DMS-RT method (left panel, lane 6) with DMS-LMPCR using either T4 DNA ligase (left panel, lane 8) or Circligase I (left panel, lane 10). The rectangles depict new bands observed only by the T4 DNA ligase method, which were not observed by the Circligase method. The gel on the right panel is a technical replicate for DMS/SHAPE-RT and DMS/SHAPE-LMPCR (using T4 DNA ligase) on 5.8S rRNA.

It is demonstrated herein, that ssDNA ligation may be used in DMS/SHAPE-LMPCR, which is a methodology that is demonstrated to increase the sensitivity in determining the structure of low-abundance transcripts. This demonstrates the utility of the ssDNA ligation compositions and methods of the present invention in various protocols, including LMPCR.

Example 3: In Vivo Genome-Wide Profiling of RNA Secondary Structure Reveals Novel Regulatory Features RNA structure has critical roles in processes ranging from ligand sensing to the regulation of translation, polyadenylation and splicing (Buratti et al., 2004, Mol Cell Biol, 24: 1387-1400; Cruz and Westhof, 2009, Cell, 136: 604-609; Kozak, 2005, Gene, 361: 13-37; Sharp, 2009, Cell, 136: 577-580). However, a lack of genome-wide in vivo RNA structural data has limited our understanding of how RNA structure regulates gene expression in living cells.

Most existing RNA structure mapping has been performed in vitro (Kertesz et al., 2010, Nature, 467: 103-107; Li et al., 2012, Plant Cell, 24: 4346-4359; Zheng et al., 2010, PLoS Genet, 6: e1001141; Wan et al., 2012, Mol Cell, 48: 169-181). Among RNA structure probing reagents, dimethyl sulphate (DMS) can penetrate cells and has been used to map structures of high-abundance RNAs in vivo in various organisms (Senecoff and Meagher, 1992, Plant Mol Biol, 18: 219-234; Wells et al., 2000, Methods, Enzymol, 318: 479-493; Zuag and Cech, 1995, RNA, 1: 363-374; Zemora and Waldsich, 2010, RNA Biol, 7: 634-641). DMS methylates the base-pairing faces of A and C of RNA in loops, bulges, mismatches and joining regions. The base-pairing status of U and G nucleotides can be inferred from structural mapping of As and Cs, because constraining even some nucleotides substantially improves predictions of other regions (Mathews et al., 2004, Proc Natl Acad Sci USA, 101: 7287-7292). However, a method for genome-wide study of RNA structure in vivo has been lacking.

As demonstrated by Ding et al., (Ding et al., 2013, Nature, November 24. doi: 10.1038/nature12756), the contents of which are incorporated by reference herein in their entirety, a high-throughput, genome-wide in vivo RNA structure probing method, Structure-Seq, was developed in which dimethyl sulfate methylation of unprotected adenines and cytosines is identified by next-generation sequencing. Application of this method to *Arabidopsis thaliana* seedlings yielded the first in vivo genome-wide RNA structure map at nucleotide resolution for any organism, with quantitative structural information across more than 10,000 transcripts. Here DMS methylation is combined with next-generation sequencing to establish Structure-Seq, an in vivo quantitative measurement of genome-wide RNA secondary structure at nucleotide resolution.

Figure 27:
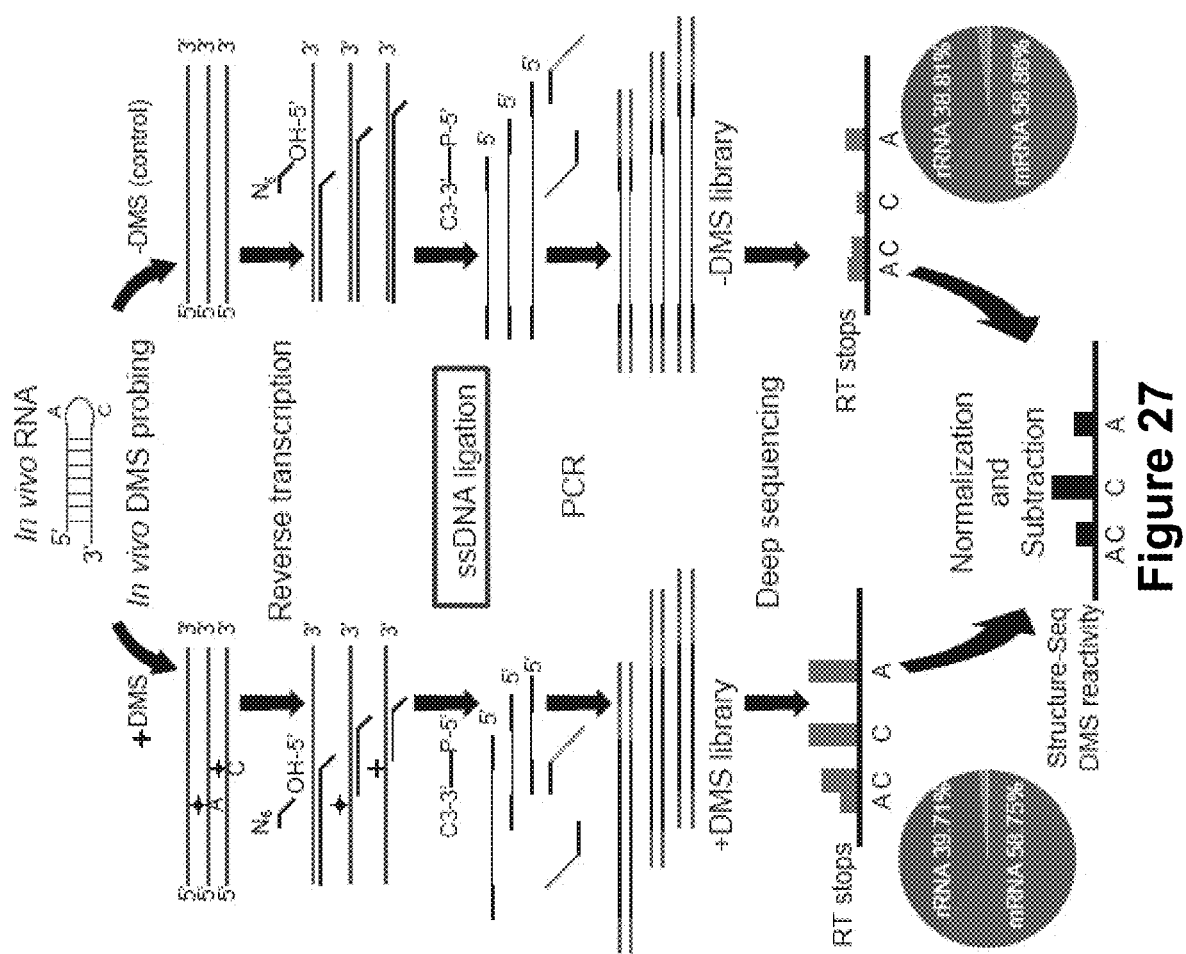
FIG. 27 depicts an overview of structure-seq. *Arabidopsis* seedlings are treated with DMS. Reverse transcription is performed using random hexamers ($N_6$) with adaptors (thicker black lines). Reverse transcriptase stalls one nucleotide before DMS-modified As and Cs (black crosses). Single-stranded (ss) DNA ligation attaches a single-stranded DNA linker (thicker black line) to the 3' end. Double-stranded DNA is generated by PCR. A (−)DMS library is prepared in parallel. Deep sequencing is performed with different indices for (+)DMS and (−)DMS libraries. Counts of the reverse transcriptase (RT) stops are normalized and subtracted. Pie charts depict percentages of RNA types for the (+)DMS (left) and (−)DMS (right) libraries. The non-rRNA and non-mRNA slice of the pie represent other RNA types plus unmappable reads

Structure-Seq, which utilizes ssDNA ligation, is now described (FIG. 27). While, the presently described experiments were conducted using *Arabidopsis* seedlings, Structure-Seq may be used to investigate any tissue or organism of interest. In the presently described experiments, *Arabidopsis* seedlings are treated with DMS. Reverse transcription is performed using random hexamers ($N_6$) with adaptors (thicker black lines). Reverse transcriptase stalls one nucleotide before DMS-modified As and Cs (black crosses) (Zuag and Cech, 1995, RNA, 1: 363-374). Single-stranded (ss) DNA ligation attaches a single-stranded DNA linker (thicker black line) to the 3' end. Double-stranded DNA is generated by PCR. A (−)DMS library is prepared in parallel. Deep sequencing is performed with different indices for (+)DMS and (−)DMS libraries. Counts of the reverse transcriptase (RT) stops are normalized and subtracted. Pie charts depict percentages of RNA types for the (+)DMS (FIG. 27, left) and (−)DMS (FIG. 27, right) libraries. The non-rRNA and non-mRNA slice represent other RNA types plus unmappable reads It was found that DMS-induced methylation sites were highly reproducible (Pearson correlation coefficient (PCC) of 0.91 for the two (+)DMS libraries). Nucleotide modification in the (+)DMS library was specific to As and Cs. Notably, 98% of the combined 206 million sequence reads were mappable to the *Arabidopsis* genome. In this experiment, the reads include diverse classes of RNAs, with a predominance of mRNAs and ribosomal RNAs. The reverse transcriptase stops are evenly distributed along the transcripts, with no 3' bias. In particular, 10,781 transcripts had sufficient coverage at nucleotide resolution to obtain secondary-structure constraints. Abundance of individual mRNAs in Structure-Seq correlated well with mRNA abundance from RNA-seq analyses (Oh et al, 2012, Nature Cell Biol, 14: 802-809).

It is demonstrated herein that ssDNA ligation can be used in Structure-Seq, a high-throughput genome-wide methodology that profiles RNA secondary structure with high accuracy and nucleotide resolution in vivo. This demonstrates the utility of the ssDNA ligation compositions and methods of the present invention in various high-throughput sequencing protocols, including Structure-Seq.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a donor nucleic acid molecule, wherein the molecule comprises a stem-loop structure and a 3' overhang, further wherein the molecule comprises a continuous primer binding site that encompasses a portion of the stem and a portion of the loop structure, wherein the donor molecule comprises a nucleotide sequence selected from the group consisting of SEQ ID NO: 5 through SEQ ID NO: 22, SEQ ID NO: 28 and SEQ ID NO: 29.

2. The composition of claim 1, wherein the stem portion of the stem-loop structure comprises at least 3 nucleotide base pairs and at least one mismatch pair.

3. The composition of claim 1, wherein the 3' overhang comprises at least 4 nucleotides.

4. The composition of claim 1, wherein the primer binding site comprises 8 nucleotides.

5. The composition of claim 1, wherein the donor molecule is hybridized to a single stranded nucleic acid acceptor molecule to form a hybridized molecule comprising the donor molecule and the acceptor molecule.

6. The composition of claim 5, wherein the hybridized molecule is stable at a temperature as high as 65° C.

7. A kit comprising a donor nucleic acid molecule, wherein the molecule comprises a stem-loop structure and a 3' overhang, further wherein the molecule comprises a continuous primer binding site that encompasses a portion of the stem and a portion of the loop structure, wherein the donor molecule comprises a nucleotide sequence selected from the group consisting of SEQ ID NO: 5 through SEQ ID NO: 22, SEQ ID NO: 28 and SEQ ID NO: 29.

8. The kit of claim 7, further comprising a DNA ligase.

9. The kit of claim 8, wherein the DNA ligase is T4 DNA ligase.

* * * * *

SEQUENCE LISTING

<160> NUMBER OF SEQ ID NOS: 31

<210> SEQ ID NO 1
<211> LENGTH: 24
<212> TYPE: DNA
<213> ORGANISM: Artificial Sequence
<220> FEATURE:
<223> OTHER INFORMATION: Chemically synthesized

<400> SEQUENCE: 1
gaaccggacc gaagcccgat ttga                                          24

<210> SEQ ID NO 2
<211> LENGTH: 24
<212> TYPE: DNA
<213> ORGANISM: Artificial Sequence
<220> FEATURE:
<223> OTHER INFORMATION: Chemically synthesized

<400> SEQUENCE: 2
gaaccggacc gaagcccgat ttgg                                          24

<210> SEQ ID NO 3
<211> LENGTH: 24
<212> TYPE: DNA
<213> ORGANISM: Artificial Sequence
<220> FEATURE:
<223> OTHER INFORMATION: Chemically synthesized

<400> SEQUENCE: 3
gaaccggacc gaagcccgat ttgc                                          24

<210> SEQ ID NO 4
<211> LENGTH: 24
<212> TYPE: DNA
<213> ORGANISM: Artificial Sequence
<220> FEATURE:
<223> OTHER INFORMATION: Chemically synthesized

<400> SEQUENCE: 4
gaaccggacc gaagcccgat ttgt                                          24

<210> SEQ ID NO 5
<211> LENGTH: 26
<212> TYPE: DNA
<213> ORGANISM: Artificial Sequence
<220> FEATURE:
<223> OTHER INFORMATION: Chemically synthesized

<400> SEQUENCE: 5
ctgctgatca ccgactgccc atagag                                        26

<210> SEQ ID NO 6
<211> LENGTH: 29
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(3)
<223> OTHER INFORMATION: n is a, c, g, or t

<400> SEQUENCE: 6
nnnctgctga tcaccgactg cccatagag                                     29

<210> SEQ ID NO 7
<211> LENGTH: 33
<212> TYPE: DNA
<213> ORGANISM: Artificial Sequence
<220> FEATURE:
<223> OTHER INFORMATION: Chemically synthesized

<400> SEQUENCE: 7
tgaagagctg ctgatcaccg actgcccata gag        33

<210> SEQ ID NO 8
<211> LENGTH: 33
<212> TYPE: DNA
<213> ORGANISM: Artificial Sequence
<220> FEATURE:
<223> OTHER INFORMATION: Chemically synthesized

<400> SEQUENCE: 8
tgaagagctg ctgatcaacg actgcccata gag        33

<210> SEQ ID NO 9
<211> LENGTH: 33
<212> TYPE: DNA
<213> ORGANISM: Artificial Sequence
<220> FEATURE:
<223> OTHER INFORMATION: Chemically synthesized

<400> SEQUENCE: 9
tgaagagctg ctgatcagcg actgcccata gag        33

<210> SEQ ID NO 10
<211> LENGTH: 33
<212> TYPE: DNA
<213> ORGANISM: Artificial Sequence
<220> FEATURE:
<223> OTHER INFORMATION: Chemically synthesized

<400> SEQUENCE: 10
tgaagagctg ctgatcatcg actgcccata gag        33

<210> SEQ ID NO 11
<211> LENGTH: 33
<212> TYPE: DNA
<213> ORGANISM: Artificial Sequence
<220> FEATURE:
<223> OTHER INFORMATION: Chemically synthesized

<400> SEQUENCE: 11
agaagagctg ctgatctccg actgcccata gag        33

<210> SEQ ID NO 12
<211> LENGTH: 33
<212> TYPE: DNA
<213> ORGANISM: Artificial Sequence
<220> FEATURE:
<223> OTHER INFORMATION: Chemically synthesized

<400> SEQUENCE: 12
ggaagagctg ctgatccccg actgcccata gag        33

<210> SEQ ID NO 13
<211> LENGTH: 33
<212> TYPE: DNA
<213> ORGANISM: Artificial Sequence
<220> FEATURE:
<223> OTHER INFORMATION: Chemically synthesized

<400> SEQUENCE: 13
cgaagagctg ctgatcgccg actgcccata gag                        33

<210> SEQ ID NO 14
<211> LENGTH: 33
<212> TYPE: DNA
<213> ORGANISM: Artificial Sequence
<220> FEATURE:
<223> OTHER INFORMATION: Chemically synthesized

<400> SEQUENCE: 14
agaagagctg ctgatcaccg actgcccata gag                        33

<210> SEQ ID NO 15
<211> LENGTH: 33
<212> TYPE: DNA
<213> ORGANISM: Artificial Sequence
<220> FEATURE:
<223> OTHER INFORMATION: Chemically synthesized

<400> SEQUENCE: 15
tgaagagctg ctgatctccg actgcccata gag                        33

<210> SEQ ID NO 16
<211> LENGTH: 33
<212> TYPE: DNA
<213> ORGANISM: Artificial Sequence
<220> FEATURE:
<223> OTHER INFORMATION: Chemically synthesized

<400> SEQUENCE: 16
tgatgagctg ctgatcaccg actgcccata gag                        33

<210> SEQ ID NO 17
<211> LENGTH: 33
<212> TYPE: DNA
<213> ORGANISM: Artificial Sequence
<220> FEATURE:
<223> OTHER INFORMATION: Chemically synthesized

<400> SEQUENCE: 17
tgacgagctg ctggtcaccg actgcccata gag                        33

<210> SEQ ID NO 18
<211> LENGTH: 33
<212> TYPE: DNA
<213> ORGANISM: Artificial Sequence
<220> FEATURE:
<223> OTHER INFORMATION: Chemically synthesized

<400> SEQUENCE: 18
tgaagagctg ctgttcaccg actgcccata gag                        33

<210> SEQ ID NO 19
<211> LENGTH: 33
<212> TYPE: DNA
<213> ORGANISM: Artificial Sequence
<220> FEATURE:
<223> OTHER INFORMATION: Chemically synthesized

<400> SEQUENCE: 19
tgaagagctg ctgttcagcg actgcccata gag                        33

```
<210> SEQ ID NO 20
<211> LENGTH: 21
<212> TYPE: DNA
<213> ORGANISM: Artificial Sequence
<220> FEATURE:
<223> OTHER INFORMATION: Chemically synthesized

<400> SEQUENCE: 20
tgaagagctg ctgttcaccg a                                         21

<210> SEQ ID NO 21
<211> LENGTH: 26
<212> TYPE: DNA
<213> ORGANISM: Artificial Sequence
<220> FEATURE:
<223> OTHER INFORMATION: Chemically synthesized

<400> SEQUENCE: 21
tgaagagcct agtcgctgtt caccga                                    26

<210> SEQ ID NO 22
<211> LENGTH: 40
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (23)..(28)
<223> OTHER INFORMATION: n is a, c, g, or t

<400> SEQUENCE: 22
tgaagagcct agtcgctgtt cannnnnnct gcccatagag                     40

<210> SEQ ID NO 23
<211> LENGTH: 16
<212> TYPE: DNA
<213> ORGANISM: Artificial Sequence
<220> FEATURE:
<223> OTHER INFORMATION: Chemically synthesized

<400> SEQUENCE: 23
cggcgaaccg gatcga                                               16

<210> SEQ ID NO 24
<211> LENGTH: 19
<212> TYPE: DNA
<213> ORGANISM: Artificial Sequence
<220> FEATURE:
<223> OTHER INFORMATION: Chemically synthesized

<400> SEQUENCE: 24
ttgtgacacc caggcagac                                            19

<210> SEQ ID NO 25
<211> LENGTH: 21
<212> TYPE: DNA
<213> ORGANISM: Artificial Sequence
<220> FEATURE:
<223> OTHER INFORMATION: Chemically synthesized

<400> SEQUENCE: 25
ccagaaggct tggggcgcaa c                                         21
```

```
<210> SEQ ID NO 26
<211> LENGTH: 91
<212> TYPE: DNA
<213> ORGANISM: Artificial Sequence
<220> FEATURE:
<223> OTHER INFORMATION: Chemically synthesized

<400> SEQUENCE: 26
ttcacaatcg cagaagctct ctcgctccag tcccctcccc cttccctccc aatttttaaa     60
agaaaataaa atcctatagt gagtcgtatt a                                    91

<210> SEQ ID NO 27
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (24)..(24)
<223> OTHER INFORMATION: n is a, c, g, or t

<400> SEQUENCE: 27
gaaccggacc gaagcccgat ttgn                                            24

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized

<400> SEQUENCE: 28
tgaagagctg ctgatcaccg a                                               21

<210> SEQ ID NO 29
<211> LENGTH: 28
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (23)..(28)
<223> OTHER INFORMATION: n is a, c, g, or t

<400> SEQUENCE: 29
tgaagagcct agtcgctgtt cannnnnn                                        28

<210> SEQ ID NO 30
<211> LENGTH: 27
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (27)..(27)
<223> OTHER INFORMATION: n may be repeated any number of times
<220> FEATURE:
<221> NAME/KEY: repeat_unit
<222> LOCATION: (27)..(27)

<400> SEQUENCE: 30
tgaacagcga ccaggctctt cannnnn                                         27
```

```
<210> SEQ ID NO 31
<211> LENGTH: 28
<212> TYPE: DNA
<213> ORGANISM: Artificial Sequence
<220> FEATURE:
<223> OTHER INFORMATION: Chemically synthesized
<220> FEATURE:
<221> NAME/KEY: repeat_unit
<222> LOCATION: (1)..(1)
<223> OTHER INFORMATION: n may be repeated any number of times
<220> FEATURE:
<221> NAME/KEY: misc_feature
<222> LOCATION: (1)..(6)
<223> OTHER INFORMATION: n is a, c, g, or t

<400> SEQUENCE: 31
nnnnnntgaa gagcctagtc gctgttca                                            28
```